US007312361B2

(12) United States Patent
Kelly et al.

(10) Patent No.: US 7,312,361 B2
(45) Date of Patent: *Dec. 25, 2007

(54) INHIBITORS OF TRANSTHYRETIN AMYLOID FIBRIL FORMATION

(75) Inventors: Jeffery W. Kelly, La Jolla, CA (US); Steven M. Johnson, San Diego, CA (US); H. Michael Petrassi, Cardiff, CA (US)

(73) Assignee: The Scripps Research Institute, La Jolla, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/350,664

(22) Filed: Feb. 8, 2006

(65) Prior Publication Data

US 2006/0178527 A1 Aug. 10, 2006

Related U.S. Application Data

(60) Provisional application No. 60/651,306, filed on Feb. 8, 2005.

(51) Int. Cl.
*C07C 243/22* (2006.01)
*C07C 251/32* (2006.01)
*C07C 229/00* (2006.01)

(52) U.S. Cl. .................. 564/251; 564/265; 562/433; 562/439

(58) Field of Classification Search ............. 564/251, 564/265; 514/639, 640; 562/433, 439
See application file for complete search history.

(56) References Cited

U.S. PATENT DOCUMENTS 4,270,947 A * 6/1981 Gutman .................... 504/303

FOREIGN PATENT DOCUMENTS

WO     2004/058747    *  7/2004

OTHER PUBLICATIONS

Aroskar et al, Journal of the Chemical Society, Sep. 1964, pp. 2975-2981.*
Miroy, et al., "Inhibiting transthyretin amyloid fibril formation via protein stabilization", *Proc. Natl. Acad. Sci. USA* 93: 15051-15056 (1996).
Peterson, et al., "Inhibiting transthyretin conformational changes that lead to amyloid fibril formation", *Proc. Natl. Acad. Sci. USA* 95: 12956-12960 (1998).
Baures, et al., "Discovering Transthyretin Amyloid Fibril Inhibitors by Limited Screening", *Bioorg. Med. Chem.* 6: 1389-1401 (1998).
Oza, et al., "Synthesis and Evaluation of Anthranilic Acid-Based Transthyretin Amyloid Fibril Inhibitors", *Bioorg. Med. Chem. Lett.* 9: 1-6 (1999).

Baures, et al., "Synthesis and Evaluation of Inhibitors of Transthyretin Amyloid Formation Based on the Non-steroidal Anti-inflammatory Drug, Flufenamic Acid", *Bioorg. Med. Chem.* 7: 1339-1347 (1999).
Petrassi, et al., "Structure-Based Design of N-Phenyl Phenoxazine Transthyretin Amyloid Fibril Inhibitors", *J. Am. Chem. Soc.* 122: 2178-2192 (2000).
Klabunde, et al., "Rational design of potent human transthyretin amyloid disease inhibitors", *Nature Struct. Biol.* 7: 312-321 (2000).
Liu, et al., "A glimpse of a possible amyloidogenic intermediate of transthyretin", *Nature Struct. Biol.* 7: 754-757 (2000).
Petrassi, et al., "The Copper-Mediated Cross-Coupling of Phenylboronic Acids and N-Hydroxyphthalimide at Room Temperature: Synthesis of Aryloxyamines", *Org. Lett.* 3: 139-142 (2001).
Purkey, et al., "Evaluating the binding selektivity of transthyretin amyloid fibril inhibitors in blood plasma", *Proc. Natl. Acad. Sci. USA* 98: 5566-5571 (2001).
Hammarström, et al., "Trans-Suppression of Misfolding in an Amyloid Disease", *Science* 293: 2459-2462 (2001).
White, et al., "Support for the multigenetic hypothesis of amyloidosis: The binding stoichiometry of retinol-binding protein, vitamin A, and thyroid hormone influences transthyretin amyloidogenicity in vitro", *Proc. Natl. Acad. Sci. USA* 98: 13019-13024 (2001).
Oza, et al., "Synthesis, Structure, and Activity of Dielofenac Analogues as Transthyretin Amyloid Fibril Formation Inhibitors", *J. Med. Chem.* 45: 321-332 (2002).
Sacchettini, et al., "Therapeutic Strategies For human Amyloid Diseases", *Nat. Rev. Drug Dis.* 1: 267-275 (2002).
Hammarström, et al., "Sequence-dependent denaturation energetics: A major determinant in amyloid disease diversity", *Proc. Natl. Acad. Sci. USA* 99: 16427-16432 (2002).
Hammarström, et al., "Prevention of Transthyretin Amyloid Disease by Changing Protein Misfolding Energetics", *Science* 299: 713-716 (2003).
Razavi, et al., "Benzoxazoles as Transthyretin Amyloid Fibril Inhibitors: Synthesis, Evaluation, and Mechanism of Action", *Angew. Chem. Int. Ed.* 42: 2758-2761 (2003).
Green, et al., "Synthesis and Characterization of Potent Bivalent Amyloidosis Inhibitors That Bind Prior to Transthyretin Tetramerization", *J. Am. Chem. Soc.* 125: 13404-13414 (2003).
Cohen, et al., "Therapeutic approaches to protein-misfolding diseases", *Nature* 426: 905-909 (2003).
Adamski-Werner, et al., "Diflunisal Analogues Stabilize the Native State of transthyretin. Potent Inhibition of Amyloidogenesis", *J. Med. Chem.* 47: 355-374 (2004).
Miller, et al., "Native state stabilization by NSAIDs inhibits transthyretin amyloidogenesis from the most common familial disease variants", *Lab. Inv.* 84: 545-552 (2004).

(Continued)

*Primary Examiner*—Shailendra Kumar
(74) *Attorney, Agent, or Firm*—Donald G. Lewis

(57) ABSTRACT

Bisaryloxime ethers and bisarylhydroazones are shown to be effective for inhibiting formation of amyloid fibrils of transthyretin.

68 Claims, 16 Drawing Sheets

OTHER PUBLICATIONS

Purkey, et al., "Hydroxylated Polychlorinated Biphenyls Selectively Bind Transthyretin in Blood and Inhibit Amyloidogenesis: Rationalizing Rodent PCB Toxicity", *Chemistry & Biology 11*: 1719-1728 (2004).

Petrassi, et al., "Potent and Selective Structure-Bases Dibenzofuran Inhibitors of Transthyretin Amyloidogenesis: Kinetic Stabilization of the Native State", *J. Am. Chem. Soc. 127*: 6662-6671 (2005).

* cited by examiner

| Arylaldehyde Component \ Arylhydrazine Component | H (22) | 2-CO₂H (23) | 3-CO₂H (24) | 4-CO₂H (25) | 2-CF₃ (26) | 3-CF₃ (27) | 3,5-Cl₂ (28) | 2,6-Cl₂ (29) |
|---|---|---|---|---|---|---|---|---|
| H (a) | 99 | 23 | 7 | 71 | 64 | 82 | 27 | 14 |
| 2-CO₂H (b) | 90 | 89 | 92 | 91 | 6 | 66 | 6 | 7 |
| 3-CO₂H (c) | 81 | 33 | 67 | 77 | 5 | 55 | 4 | 0 |
| 4-CO₂H (d) | 59 | 18 | 56 | 74 | 5 | 66 | 12 | 0 |
| 3,5-I₂,4-OH (e) | 8 | 4 | 2 | 0 | 1 | 1 | 1 | 0 |
| 3,5-Br₂,4-OH (f) | 1 | 3 | 1 | 0 | 3 | 0 | 3 | 0 |
| 2-CF₃ (g) | 50 | 2 | 7 | 12 | 37 | 40 | 25 | 8 |
| 3-CF₃ (h) | 82 | 5 | 44 | 66 | 74 | 72 | 24 | 19 |
| 4-CF₃ (i) | 93 | 66 | 73 | 85 | 83 | 100 | 62 | 50 |
| 3,5-F₂ (j) | 76 | 2 | 30 | 50 | 81 | 68 | 29 | 26 |
| 3,5-Cl₂ (k) | 2 | 0 | 0 | 0 | 80 | 19 | 26 | 18 |
| 2,6-Cl₂ (l) | 19 | 0 | 2 | 0 | 5 | 28 | 4 | 9 |

Legend: 0-10% Good | 11-30% Moderate | >30% Poor

Figure 4

| Compound | Purity | Compound | Purity | Compound | Purity | Compound | Purity |
|---|---|---|---|---|---|---|---|
| 1e | 96% | 2a | >99% | 3a | 98% | 4a | 97% |
| 5d | 98% |  |  | 3b | >99% | 4b | 99% |
| 5e | 95% | 2c | >99% | 3c | 98% | 4c | 96% |
| 5f | 97% | 2d | 98% | 3d | >99% | 4d | 95% |
| 7e | 96% | 2e | 96% | 3e | 98% | 4e | 95% |
| 8e | 97% | 2f | >99% | 3f | 95% | 4f | 96% |
| 8f | >99% | 2g | 99% | 3g | 99% | 4g | 99% |
|  |  | 2h | 98% | 3h | >99% | 4h | 98% |
|  |  | 2i | 95% | 3i | 97% | 4i | >99% |
|  |  | 2j | 96% | 3j | 97% | 4j | 96% |
|  |  | 2k | 99% | 3k | 98% | 4k | 99% |
|  |  | 2l | 99% | 3l | >99% | 4l | 95% |

Figure 8

| Arylaldehyde Component \ Aryloxyamine Component | H (1) | 2-CO$_2$H (2) | 3-CO$_2$H (3) | 4-CO$_2$H (4) | 2-CF$_3$ (5) | 3-CF$_3$ (6) | 3,5-Cl$_2$ (7) | 3,5-F$_2$ (8) |
|---|---|---|---|---|---|---|---|---|
| H (a) | 96 | 91 | 50 | 32 | 56 | 83 | 39 | 87 |
| 2-CO$_2$H (b) | 91 | Unstable | 94 | 97 | 75 | 84 | 30 | 84 |
| 3-CO$_2$H (c) | 79 | 87 | 15 | 13 | 6 | 9 | 3 | 6 |
| 4-CO$_2$H (d) | 77 | 87 | 31 | 46 | 3 | 12 | 9 | 9 |
| 3,5-I$_2$,4-OH (e) | 0 | 0 | 0 | 1 | 1 | 4 | 4 | 3 |
| 3,5-Br$_2$,4-OH (f) | 0 | 0 | 0 | 0 | 1 | 4 | 3 | 3 |
| 2-CF$_3$ (g) | 65 | 34 | 1 | 0 | 83 | 83 | 32 | 71 |
| 3-CF$_3$ (h) | 92 | 74 | 27 | 50 | 57 | 83 | 55 | 86 |
| 4-CF$_3$ (i) | 98 | 90 | 83 | 94 | 81 | 93 | 68 | 77 |
| 3,5-F$_2$ (j) | 95 | 78 | 8 | 18 | 75 | 88 | 61 | 94 |
| 3,5-Cl$_2$ (k) | 56 | 1 | 0 | 9 | 33 | 72 | 63 | 90 |
| 2,6-Cl$_2$ (l) | 63 | 59 | 1 | 0 | 15 | 21 | 62 | 24 |

Legend: 0–10% Good | 11–30% Moderate | >30% Poor

Figure 10

|  | % Inhibitor Remaining | |
| --- | --- | --- |
| Inhibitor | Without TTR | With TTR |
| 1e | 24 | 79 |
| 1f | 8 | 76 |
| 2k | 4 | 74 |
| 3e | 81 | 77 |
| 3g | 20 | 88 |
| 4e | 91 | 83 |
| 4f | 88 | 81 |
| 4g | 79 | 84 |
| 4l | 85 | 81 |
| 5d | 80 | 83 |
| 5d* | 0 | 76 |
| 5e | 89 | 100 |
| 5f | 78 | 98 |

Figure 11

| | R' Substituent | | | |
|---|---|---|---|---|
| | CHO | CN | OH | NH₂ |
| H | 99 | 94 | 100 | 97 |
| 2-CO₂H | 99 | 92 | 92 | 98 |
| 3-CO₂H | 98 | 91 | 97 | 100 |
| 4-CO₂H | 90 | 86 | 95 | 98 |
| 3,5-I₂,4-OH | 1 | 0 | | |
| 3,5-Br₂,4-OH | 1 | 0 | | |
| 2-CF₃ | 95 | 87 | 77 | 95 |
| 3-CF₃ | 87 | 94 | 80 | 97 |
| 4-CF₃ | 88 | 100 | | |
| 3,5-DiF | 94 | 90 | 95 | |
| 3,5-DiCl | 79 | 88 | 14 | 70 |
| 2,6-DiCl | 92 | 81 | | 90 |

Legend: 0-10% Good | 11-30% Moderate | >30% Poor

| Arylaldehyde Component \ Aryloxyamine Component | H (1) | 2-CO₂H (2) | 3-CO₂H (3) | 4-CO₂H (4) | 2-CF₃ (5) | 3-CF₃ (6) | 3,5-Cl₂ (7) | 3,5-F₂ (8) |
|---|---|---|---|---|---|---|---|---|
| 3-CO₂H (c) | 0.89 | | | | 1.07 | <0.5 | 0.56 | <0.5 |
| 4-CO₂H (d) | 1.02 | | | | 1.38 | | 0.78 | <0.5 |
| 3,5-I₂,4-OH (e) | | <0.5 | <0.5 | <0.5 | 1.71 | 1.02 | 0.55 | 1.83 |
| 3,5-Br₂,4-OH (f) | | <0.5 | <0.5 | <0.5 | 1.86 | 1.17 | 0.69 | 1.42 |
| 2-CF₃ (g) | | | 1.00 | 1.31 | | | | |
| 3,5-F₂ (j) | | | <0.5 | | | | | |
| 3,5-Cl₂ (k) | | <0.5 | <0.5 | 0.53 | | | | |
| 2,6-Cl₂ (l) | | | 0.71 | 0.81 | | | | |

Legend:
| >1.5 eq Excellent | 1.0-1.5 eq Good | 0.5-1.0 eq Moderate | <0.5 eq Poor |
|---|---|---|---|

Figure 15

|  | TTR•(5d)$_2$ |
|---|---|
| Resolution (Å) | 27.385-1.53 |
| No. of unique reflections | 33585 |
| Completeness (%) (overall/outer shell) | 92.3 / 85.7 |
| Rsym (overall/outer shell) | 0.06 / 0.12 |
| R-factor/R-free (%) | 22.8 / 26.1 |
| RMS Deviations | |
|     Bond length (Å) | 0.05 |
|     Bond angles (°) | 2.3 |

Figure 17

INHIBITORS OF TRANSTHYRETIN AMYLOID FIBRIL FORMATION

This invention was made with United States Government support under Contract Nos. GM28384 AND DK46335 by the National Institutes of Health. The United States Government has certain rights in the invention.

This application claims benefit of 60/651,306, filed Feb. 8, 2005.

TECHNICAL FIELD

The present invention relates to inhibitors of transthyretin amyloid fibril formation. More particularly, the invention relates to bisaryloxime ethers as inhibitors of transthyretin amyloid fibril formation.

BACKGROUND

The process of transthyretin (TTR) amyloidogenesis leads to peripheral neuropathy, organ dysfunction, and in rare cases central nervous system pathology (Sekijima, Y.; et al. *Lab. Invest.* 2003, 83, 409-417; Hammarström, P.; et al. *Biochemistry*, 2003, 42, 6656-6663; Garzuly, F.; et al. *Neurology*, 1996, 47, 1562-1567; Ikeda, S.; et al. *Neurology*, 2002, 58, 1001-1007; Westermark, P.; et al. *Proc. Natl. Acad. Sci. U.S.A.* 1990, 87, 2843-2845; Jacobson, D. R.; et al. *N. Engl. J. Med.* 1997, 336, 466-473; Sipe, J. D. *Crit. Rev. Clin. Lab. Sci.* 1994, 31, 325-354). The disease caused by wild type (WT) TTR deposition, senile systemic amyloidosis (SSA), is a late onset cardiomyopathy affecting 10-25% of the population over age 80 (Westermark, P.; et al. *Proc. Natl. Acad. Sci. U.S.A.* 1990, 87, 2843-2845). The remaining TTR-based amyloid diseases associated with point mutations are grouped into two broad classifications: familial amyloid cardiomyopathy (FAC) (Jacobson, D. R.; et al. *N. Engl. J. Med.* 1997, 336, 466-473) and familial amyloid polynueropathy (FAP) (Sipe, J. D. *Crit. Rev. Clin. Lab. Sci.* 1994, 31, 325-354). There are over 100 TTR mutations that cause the familial amyloidoses, the exact age of onset, tissue selectivity, and severity of which are dependent on the energetics of the specific mutation, the individual's genetic background, and possibly environmental factors (White, J. T.; Kelly, J. W. *Proc. Natl. Acad. Sci. U.S.A.* 2001, 98, 13019-13024; Hammarström, P.; et al. *Proc. Natl. Acad. Sci. U.S.A.* 2002, 99, 16427-16432).

The only treatment currently available for FAP is gene therapy mediated by surgical replacement of the patient's liver, the organ secreting TTR subject to misfolding into the blood stream (Herlenius, G.; et al. *Transplantation* 2004, 77, 64-71). The disadvantages of this approach include its invasiveness for both the donor and recipient, the requirement for life-long immune suppression, and the limited effectiveness for some mutations for reasons that are not yet clear (Olofsson, B.-O.; et al. *Transplantation* 2002, 73, 745-751). Currently there is no effective treatment for SSA associated with WT-TTR deposition. Therefore, a generally applicable, small molecule therapeutic strategy for all TTR-based amyloid diseases would be welcomed.

Interallelic trans-suppression in a compound heterozygous family enabled by the inclusion of T119M transthyretin subunits into tetramers otherwise composed of disease associated subunits (V30M), demonstrates that kinetic stabilization of TTR is sufficient to ameliorate FAP (Hammarström, P.; et al. *Science* 2003, 299, 713-716; Coelho, T.; et al. *J. Rheumatol.* 1993, 20, 179; Coelho, T.; et al. *Neuromusc. Disord.* 1996, 6, 27). The efficacy of trans-suppression implies that small molecule native state kinetic stabilization should also ameliorate amyloidosis (Sacchettini, J. C.; Kelly, J. W. *Nat. Rev. Drug Disc.* 2002, 1, 267-275; Cohen, F. E.; Kelly, J. W. *Nature* 2003, 426, 6968, 905-909). The utility of small molecules to tune the free energy landscape of proteins to prevent misfolding associated with disease has now been demonstrated in several instances (Hammarström, P.; et al. *Science* 2003, 299, 713-716; Saccheftini, J. C.; Kelly, J. W. *Nat. Rev. Drug Disc.* 2002, 1, 267-275; Cohen, F. E.; Kelly, J. W. *Nature* 2003, 426, 6968, 905-909; De Lorenzi, E.; et al. *Curr. Med. Chem.* 2004, 11, 1065-1084; Hardy, J.; et al. *Science* 2002, 297, 353-356; Ray, S. S.; Lansbury, P. T., Jr. *Proc. Natl. Acad. Sci. U.S.A.* 2004, 101, 5701-5702; Miller, S. R.; Sekijima, Y.; Kelly, J. W. *Lab. Invest.* 2004, 84, 545-552).

TTR is a 127-residue β-sheet rich homotetramer characterized by 222 molecular symmetry, possessing two thyroxine ($T_4$) binding sites (Blake, C. C.; et al. *J. Mol. Biol.* 1974, 88, 1-12; Blake, C. C.; et al. *J. Mol. Biol.* 1978, 121, 339-56). The vast majority (>99%) of the TTR $T_4$ binding capacity in both the cerebrospinal fluid (CSF) and blood plasma is unutilized because of the high concentration of TTR and the presence of thyroid binding globulin (blood) and albumin (blood and CSF), which are also carriers of T4 (Bartalena, L.; Robbins, J. *Clin. Lab. Med.* 1993, 13, 583-598; Schreiber, G.; Richardson, S. J. *Comp. Biochem. Physiol. B Biochem. Mol. Biol.* 1997, 116, 137-160; Stockigt, J. R. Thyroid Hormone Binding and Metabolism. *Endocrinology, Fourth Ed.* Degroot, L. J., Jameson, J. L., Eds.; W.B. Saunders Co.: Philadelphia, 2001, Volume 2, Chapter 94, 1314-1326). Rate-limiting tetramer dissociation is required for amyloidogenesis (Colon, W.; Kelly, J. W. *Biochemistry* 1992, 31, 8654-8660; Hammarström, P.; et al. *Science* 2001, 293, 2459-2462; Lai, Z.; Colon, W.; Kelly, J. W. *Biochemistry* 1996, 35, 6470-6482; Lashuel, H. A.; Lai, Z.; Kelly, J. W. *Biochemistry* 1998, 37, 17851-17864), but is not sufficient (Jiang, X.; et al. *Biochemistry* 2001, 40, 11442-11452), as the resulting folded monomer must also undergo partial denaturation to misassemble (Colon, W.; Kelly, J. W. *Biochemistry* 1992, 31, 8654-8660; Lai, Z.; Colon, W.; Kelly, J. W. Biochemistry 1996, 35, 6470-6482; Lashuel, H. A.; Lai, Z.; Kelly, J. W. *Biochemistry* 1998, 37, 17851-17864; Jiang, X.; et al. *Biochemistry* 2001, 40, 11442-11452; Liu, K.; et al. *Nat. Struct. Biol.* 2000, 7, 754-757). Previous studies demonstrate that $T_4$ binding inhibits TTR aggregation by kinetic stabilization of the native state. The activation barrier for dissociation is increased by preferential stabilization of the native tetramer relative to the dissociative transition state (Hammarström, P.; et al. *Science* 2003, 299, 713-716; Miroy, G. J.; et al. *Proc. Natl. Acad. Sci. U.S.A.* 1996, 93, 15051-15056; Peterson, S. A.; et al. *Proc. Natl. Acad. Sci. U.S.A.* 1998, 95, 12956-12960).

Screening, structure-based design, and lead compound optimization by parallel synthesis has led to several other structurally distinct classes of potent TTR amyloidogenesis inhibitors (Hammarström, P.; et al. *Science* 2003, 299, 713-716; Sacchettini, J. C.; Kelly, J. W. *Nat. Rev. Drug Disc.* 2002, 1, 267-275; Cohen, F. E.; Kelly, J. W. *Nature* 2003, 426, 6968, 905-909; Miller, S. R.; Sekijima, Y.; Kelly, J. W. *Lab. Invest.* 2004, 84, 545-552; Miroy, G. J.; et al. *Proc. Natl. Acad. Sci. U.S.A.* 1996, 93, 15051-15056; Peterson, S. A.; et al. *Proc. Natl. Acad. Sci. U.S.A.* 1998, 95, 12956-12960; Petrassi, H. M.; et al. *J. Am. Chem. Soc.* Submitted; Purkey, H. E.; et al. *Chemistry & Biology*. In press; Adamski-Werner, S. L.; et al. *J. Med. Chem.* 2004, 47, 355-374; Green, N. S.; et al. *J. Am. Chem. Soc.* 2003, 125, 13404-

13414; Petrassi, H. M.; et al. *J. Am. Chem. Soc.* 2000, 122, 2178-2192; Baures, P. W.; et al. *Bioorg. Med. Chem.* 1998, 6, 1389-1401; Oza, V. B.; et al. *Bioorg. Med. Chem. Lett.* 1999, 9, 1-6; Baures, P. W.; et al. *Bioorg. Med. Chem.* 1999, 7, 1339-1347; Klabunde, T.; et al. *Nat. Struct. Biol.* 2000, 7, 312-321; Oza, V. B.; et al. *J. Med. Chem.* 2002, 45, 321-332; Razavi, H.; et al. *Angew. Chem. Int. Ed.* 2003, 42, 2758-2761). Effective inhibitors generally have two aryls linked directly or through a spacer such as an amine, an ether, or an ethylene bridge. Optimally, one aryl is functionalized with halogens or aliphatic groups (typically occupying the inner cavity of the thyroxine binding site), and the other by a hydroxyl and/or carboxylic acid (which can interact electrostatically with the Lys-15 e-$NH_3^+$ and/or Glu-54 carboxyl groups at the periphery of the outer binding cavity) (Hammarström, P.; et al. *Science* 2003, 299, 713-716; Sacchettini, J. C.; Kelly, J. W. *Nat. Rev. Drug Disc.* 2002, 1, 267-275; Cohen, F. E.; Kelly, J. W. *Nature* 2003, 426, 6968, 905-909; Miller, S. R.; Sekijima, Y.; Kelly, J. W. *Lab. Invest.* 2004, 84, 545-552; Miroy, G. J.; et al. *Proc. Natl. Acad. Sci. U.S.A.* 1996, 93, 15051-15056; Peterson, S. A.; et al. *Proc. Natl. Acad. Sci. U.S.A.* 1998, 95, 12956-12960; Petrassi, H. M.; et al. *J. Am. Chem. Soc.* Submitted; Purkey, H. E.; et al. *Chemistry & Biology*. In press; Adamski-Werner, S. L.; et al. *J. Med. Chem.* 2004, 47, 355-374; Green, N. S.; et al. *J. Am. Chem. Soc.* 2003, 125, 13404-13414; Petrassi, H. M.; et al. *J. Am. Chem. Soc.* 2000, 122, 2178-2192; Baures, P. W.; et al. *Bioorg. Med. Chem.* 1998, 6, 1389-1401; Oza, V. B.; et al. *Bioorg. Med. Chem. Lett.* 1999, 9, 1-6; Baures, P. W.; et al. *Bioorg. Med. Chem.* 1999, 7, 1339-1347; Klabunde, T.; et al. *Nat. Struct. Biol.* 2000, 7, 312-321; Oza, V. B.; et al. *J. Med. Chem.* 2002, 45, 321-332; Razavi, H.; et al. *Angew. Chem. Int. Ed.* 2003, 42, 2758-2761). Both cavities have hydrophobic depressions called halogen binding pockets, that are complemented by the aryl substructures and their hydrophobic substituents.

After considering the orientation and placement of substituted aromatics in numerous TTR.(inhibitor)$_2$ co-crystal structures, synthetic accessibility, and the potential for future high-throughput dynamic combinatorial library analyses (Nazarpack-Kandlousy, N.; et al. *J. Comb. Chem.* 1999, 199-206; Hochgürtel, M.; et al. *Proc. Nat. Acad. Sci., U.S.A.* 2002, 99, 3382-3387), we chose to explore the aldoxime ether moiety to link the two aryl rings. There are several FDA approved antibacterial agents containing the oxime ether moiety, suggesting that this substructure is compatible with human biology (FDA approved antibacterial agents containing the oxime ether moiety were found using MDL ISIS/Base 2.5, from MDL Information Systems, Inc., MDDR 2003.2 (25.11) database, which scans the Drug Data Report from Prous Science Publishers containing data regarding the development of pharmaceuticals.). The goal of this study is to find bisarylaldoxime ether structures that bind with high affinity to TTR in human blood plasma (Purkey, H. E.; et al. *Proc. Natl. Acad. Sci. U.S.A* 2001, 98, 5566-5571) and stabilize the native state against amyloidogenesis (Hammarström, P.; et al. *Science* 2003, 299, 713-716; Cohen, F. E.; Kelly, J. W. *Nature* 2003, 426, no. 6968, 905-909).

SUMMARY

Amyloid fibril formation by the plasma protein transthyretin (TTR), requiring rate limiting tetramer dissociation and monomer misfolding, is implicated in several human diseases. Amyloidogenesis can be inhibited through native state stabilization, mediated by small molecule binding to TTR's primarily unoccupied thyroid hormone binding sites. New native state stabilizers have been discovered herein by the facile condensation of arylaldehydes with aryloxyamines affording a bisarylaldoxime ether library. Of the library's 95 compounds, 31 were active inhibitors of TTR amyloid formation in vitro. The bisaryloxime ethers selectively stabilize the native tetrameric state of TTR over the dissociative transition state under amyloidogenic conditions, leading to an increase in the dissociation activation barrier. Several bisaryloxime ethers bind selectively to TTR in human blood plasma over the plethora of other plasma proteins, a necessary attribute for efficacy in vivo. While bisarylaldoxime ethers are susceptible to degradation by N—O bond cleavage, this process is slowed by their binding to TTR. Furthermore, the degradation rate of many of the bisarylaldoxime ethers is slow relative to the half-life of plasma TTR. The bisaryloxime ether library provides valuable structure-activity relationship insight for the development of structurally analogous inhibitors with superior stability profiles, should that prove necessary.

One aspect of the invention is directed to a bisaryloxime ether or bisarylhydroazone represented by formula I as follows:

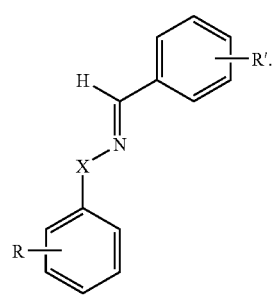

(Formula I)

In Formula I, R' is either absent or is one or more radicals selected from the group consisting of —COOH, —OH, —F, —I, —Br, —Cl, and $CF_3$; R is either absent or is one or more radicals selected from the group consisting of —COOH, —F, —Cl, and $CF_3$; and X is a diradical selected from the group constisting of —NH— and —O—. In a preferred embodiment, X is —O—; in another preferred embodiment, X is —NH—. In a further preferred embodiment, the bisaryloxime ether or bisarylhydroazone is represented by formula II as follows:

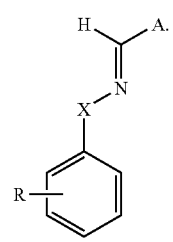

(Formula II)

In the Formula II, the radical A is selected from the following group:

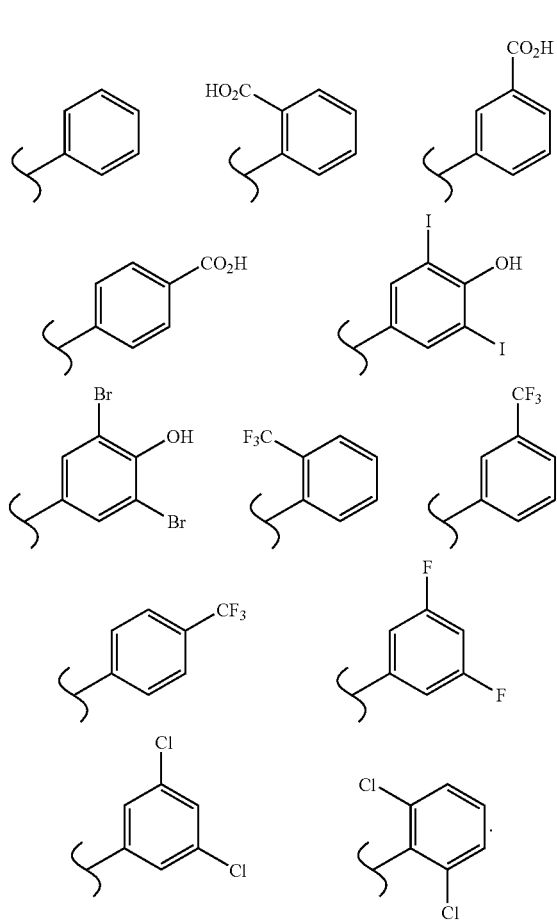

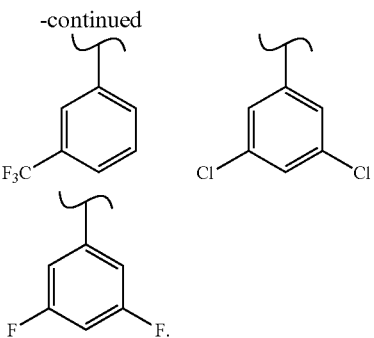

In a further preferred embodiment, the bisaryloxime ether or bisarylhydroazone is represented by formula III as follows:

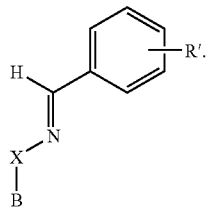

(Formula III)

In Formula III, the radical B is selected from the following group:

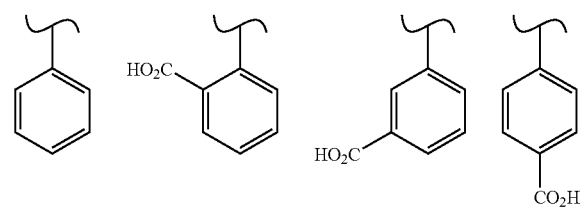

Another aspect of the invention is directed to a process for inhibiting a formation of amyloid fibrils of transthyretin. The process comprises the step of contacting the transthyretin with an inhibiting concentration of a bisaryloxime ether or bisarylhydroazone of Formulas I, II, or III.

BRIEF DESCRIPTION OF FIGURES

FIG. 4 illustrates a table showing the activities of the 96 bisarylhydrazones that were tested for inhibition of fibril formation.

FIG. 8 illustrates a table of the RP-HPLC purity of oxime ethers synthesized conventionally and isolated in mg quantities.

FIG. 10 illustrates a table summarizing the inhibitory activity of the oxime ethers (7.2 mM) against acid-mediated (pH 4.4) TTR (3.6 mM) amyloid formation.

FIG. 11 illustrates a table showing the percent oxime ether inhibitor remaining at the conclusion of the acid-mediated fibril formation assay (72 h).

FIG. 15 illustrates table showing the lower limits of the binding stoichiometry of bisaryloxime ethers displaying <90% amyloid inhibition (7.2 μM) to plasma TTR.

FIG. 17 illustrates the X-ray crystal structure data for WT-TTR soaked with oxime ether 5d.

DETAILED DESCRIPTION

X-ray crystallographic analysis of analogous bisaryloxime ethers and bisarylhydrazones show that they are isostructural. Of the 95 member oxime ether library synthesized, based on the hydrazone library activity, nearly ⅓ are excellent TTR amyloidogenesis inhibitors at a concentration of 7.2 µM, twice that of tetrameric WT-TTR (>90% inhibition at pH 4.4, over 72 h). The best inhibitors have one aromatic ring substituted with a carboxylic acid, while the other aryl ring bears halogens or a trifluoromethyl group. The oxime ethers prepared from arylaldehydes with a thyroxine-like substitution pattern also exhibit excellent activity and notable TTR plasma binding selectivity: several display binding stoichiometries exceeding 1.5 of 2. The oxime ethers not only selectively stabilize TTR's native state relative to the dissociative transition state, substantially slowing tetramer dissociation and amyloidosis, but by virtue of TTR binding their degradation is notably slowed relative to just buffer, in cases where the bisaryloxime ethers exhibited lability.

Figure 1:
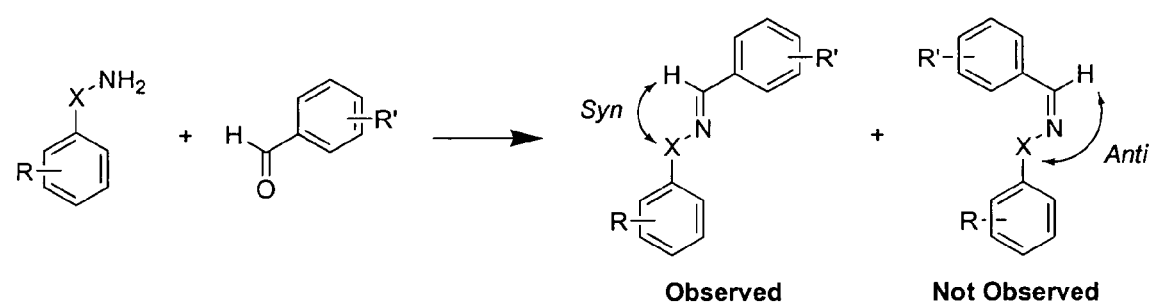
FIG. 1 illustrates a scheme showing the general approach for the formation of the bisaryloxime ether (X=O) and bisarylhydrazone (X=NH) libraries.

Design of the oxime ether library. Aryloxyamines are required as starting materials to couple with arylaldehydes to generate the desired bisaryloxime ether library (FIG. 1, X=O). This reaction could potentially produce two stereoisomers about the imine linkage (denoted syn and anti, i.e. the aldehyde proton could be oriented cis or trans, respectively, to the phenoxy oxygen represented by X, FIG. 1); however, only the syn-isomer was expected (and observed, see below) based on literature precedent (Karabatsos, G. J.; et al. *J. Am. Chem. Soc.* 1962, 84, 753-755; Lustig, E. *J. Phys. Chem.* 1961, 65, 491-495; Karabatsos, G. J.; et al. *J. Am. Chem. Soc.* 1963, 85, 2784-2788; Karabatsos, G. J.; Taller, R. A. *J. Am. Chem. Soc.* 1963, 85, 3624-3629; Sheradsky, T.; Nov, E. *J. Chem. Soc. Perkin Trans. I* 1980, 12, 2781-2786; Karabatsos, G. J.; His, N. *Tetrahedron* 1967, 23, 1079-1095; Rappoport, Z.; Sheradsky, T. *J. Chem. Soc. B, Phys. Org.* 1967, 9, 898-903).

The oxime ether substituents and substitution patterns were chosen based upon structural features identified in other potent TTR amyloidogenesis inhibitors (FIG. 2) (Hammarström, P.; et al. *Science* 2003, 299, 713-716; Sacchettini, J. C.; Kelly, J. W. *Nat. Rev. Drug Disc.* 2002, 1, 267-275; Cohen, F. E.; Kelly, J. W. *Nature* 2003, 426, 6968, 905-909; Miller, S. R.; Sekijima, Y.; Kelly, J. W. *Lab. Invest.* 2004, 84, 545-552; Miroy, G. J.; et al. *Proc. Natl. Acad. Sci. U.S.A.* 1996, 93, 15051-15056; Peterson, S. A.; et al. *Proc. Natl. Acad. Sci. U.S.A.* 1998, 95, 12956-12960; Petrassi, H. M.; et al. *J. Am. Chem. Soc.* Submitted; Purkey, H. E.; et al. *Chemistry & Biology*. In press; Adamski-Werner, S. L.; et al. *J. Med. Chem.* 2004, 47, 355-374; Green, N. S.; et al. *J. Am. Chem. Soc.* 2003, 125, 13404-13414; Petrassi, H. M.; et al. *J. Am. Chem. Soc.* 2000, 122, 2178-2192; Baures, P. W.; et al. *Bioorg. Med. Chem.* 1998, 6, 1389-1401; Oza, V. B.; et al. *Bioorg. Med. Chem. Lett.* 1999, 9, 1-6; Baures, P. W.; et al. *Bioorg. Med. Chem.* 1999, 7, 1339-1347; Klabunde, T.; et al. *Nat. Struct. Biol.* 2000, 7, 312-321; Oza, V. B.; et al. *J. Med. Chem.* 2002, 45, 321-332; Razavi, H.; et al. *Angew. Chem. Int. Ed.* 2003, 42, 2758-2761). The aryloxyamines chosen (1-8) had the same substitution patterns as the arylaldehydes, except for the absence of para-$CF_3$ (i) and the thyroxine-like substitution patterns (e and f) in the aryloxyamines. Unfortunately, the only commercially available aryloxyamine is phenoxyamine; thus, methodology for the synthesis of the aryloxyamine building blocks required to prepare the bisaryloxime ether library are described herein and elsewhere (Abele, E.; Lukevics, E. *Org. Prep. Proced. Int.* 2000, 32, 235-264; Petrassi, H. M.; Sharpless, K. B.; Kelly, J. W. *Org. Lett.* 2001, 3, 139-142; Miyazawa, E.; et al. *Org. Prep. Proced. Int.* 1997, 29, 594-600; Choong, I. C.; Ellman, J. A. *J. Org. Chem.* 1999, 64, 6528-6529). In contrast, over 150 arylhydrazines are commercially available for coupling to readily available arylaldehydes to produce a bisarylhydrazone library (FIG. 1, X=NH). Because analogous bisaryloxime ethers and bisarylhydrazones (hereafter referred to as oxime ethers and hydrazones, respectively) were assumed to be isostructural with one another, the rapid automated synthesis of a hydrazone library (FIG. 3) was performed to query whether this structural class of inhibitors would likely be active (FIG. 4).

Figure 5:
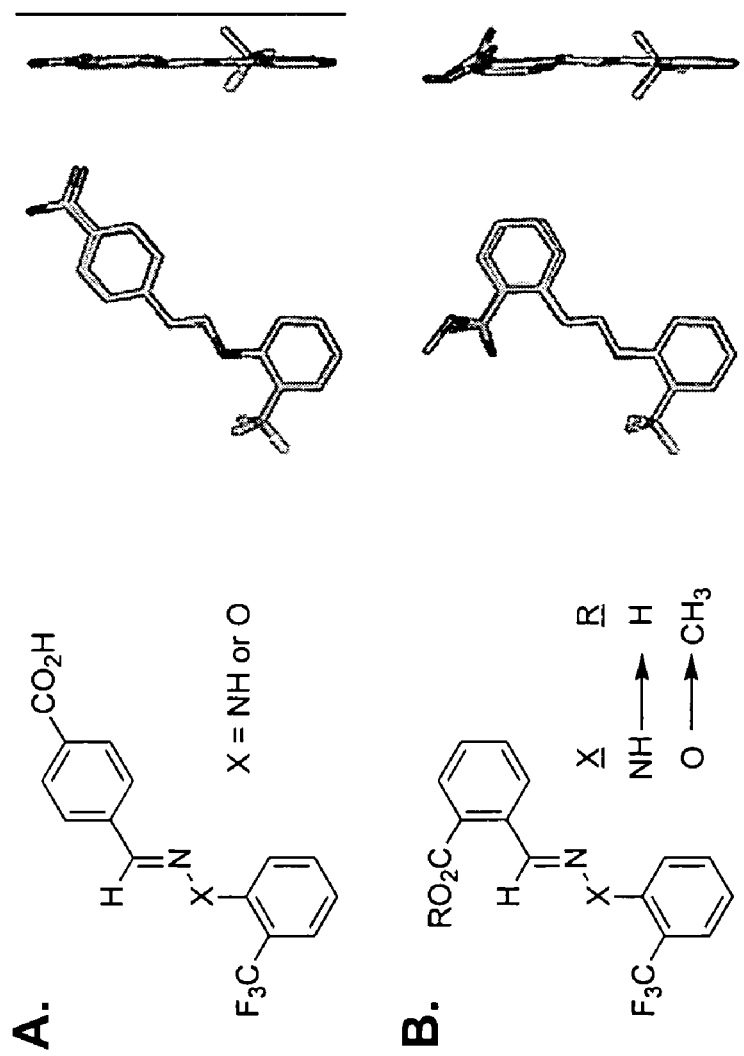
FIG. 5 illustrates the structures of the oxime ether and hydrazone inhibitors.

Characterization of and Crystallographic Comparison of Oxime Ethers and Hydrazones. To confirm their presumed isostructural nature, pairs of analogous oxime ethers and hydrazones based on scaffolds 5b/d (FIG. 2) and 26b/d (FIG. 3), respectively, were synthesized, crystallized, and their structures determined by X-ray diffraction. Comparison of the oxime ether and hydrazone structures by crystallography reveal that the analogous compounds are nearly superimposable on one another (FIG. 5). All four crystal structures display syn-imine linkages, further supporting the predominance of this isomer (Karabatsos, G. J.; et al. *J. Am. Chem. Soc.* 1962, 84, 753-755; Lustig, E. *J. Phys. Chem.* 1961, 65, 491-495; Karabatsos, G. J.; et al. *J. Am. Chem. Soc.* 1963, 85, 2784-2788; Karabatsos, G. J.; Taller, R. A. *J. Am. Chem. Soc.* 1963, 85, 3624-3629; Sheradsky, T.; Nov, E. *J. Chem. Soc. Perkin Trans. I* 1980, 12, 2781-2786; Karabatsos, G. J.; His, N. *Tetrahedron* 1967, 23, 1079-1095; Rappoport, Z.; Sheradsky, T. *J. Chem. Soc. B, Phys. Org.* 1967, 9, 898-903).

HPLC and LC-MS traces of all the crude reaction mixtures associated with hydrazone (>94% purity) and oxime ether (>95% purity) library production showed primarily one peak, suggesting the predominance of a single isomer (syn-imine linkage inferred from precedent and supported by X-ray crystallography). In principle it is possible that both the syn- and the anti-isomers co-elute or rapidly interconvert, and crystallize preferentially as the syn-isomer; however, the $^1$H- and $^{13}$C-NMR spectra of the hydrazones and oxime ethers synthesized by traditional means exhibit resonances consistent with a single isomer (literature precedence demonstrates that the preferred syn-isomer is distinguishable from the trans- by NMR at room temperature) (Karabatsos, G. J.; et al. *J. Am. Chem. Soc.* 1962, 84, 753-755; Lustig, E. *J. Phys. Chem.* 1961, 65, 491-495; Karabatsos, G. J.; et al. *J. Am. Chem. Soc.* 1963, 85, 2784-2788; Karabatsos, G. J.; Taller, R. A. *J. Am. Chem. Soc.* 1963, 85, 3624-3629; Sheradsky, T.; Nov, E. *J. Chem. Soc. Perkin Trans. I* 1980, 12, 2781-2786; Karabatsos, G. J.; His, N. *Tetrahedron* 1967, 23, 1079-1095).

Synthesis and Activity of Oxime Ether Library. Since the hydrazones (all >94% purity) displayed inhibitory activity, it was assumed that the equivalent oxime ether library would also produce TTR amyloidogenesis inhibitors. The assumption is confirmed herein. Several of the bisarylhydrazones displayed potent inhibition of TTR amyloidogenesis (FIG. 4), justifying the preparation and evaluation of an analogous oxime ether library. Aqueous hydrazone instability (owing primarily to Schiff base hydrolysis) and the biological toxicity of hydrazones provide further incentive to prepare the bisaryloxime ether library. Two synthetic strategies were employed for the preparation of the aryloxyamines required to make the bisaryloxime ether library. In the first, a copper-mediated cross-coupling of N-hydroxyphthalimide (NHP) with arylboronic acids affords the desired aryloxyamines after hydrazinolysis (FIG. 6) (Petrassi, H. M.; Sharpless, K. B.; Kelly, J. W. Org. Lett. 2001, 3, 139-142). Aryloxyamines isolated as either free bases (3, 6, and 7) or precipitated as their hydrochloride salts (1 and 8) were synthesized in good to moderate overall yields using this methodology.

The copper-mediated coupling methodology appears to be intolerant of ortho-halide or ortho-$CF_3$ substituents on the arylboronic acid (Petrassi, H. M.; Sharpless, K. B.; Kelly, J. W. Org. Lett. 2001, 3, 139-142). Furthermore, hydrazinolysis, required for the deprotection of the N-hydroxyphthalimide intermediates, does not succeed for aryloxyamines bearing ortho-carboxyl substituents. After exploring several other methods, the nucleophilic aromatic substitution of electron deficient flourobenzenes by ethyl-N-hydroxyacetimidate was selected to complement the first method (FIG. 7) (Miyazawa, E.; et al. Org. Prep. Proced. Int. 1997, 29, 594-600). Nucleophilic attack of ethyl-N-hydroxyacetimidate on 2-trifluoromethylflourobenzene gave an excellent yield of 15 (89%), which upon acidic hydrolysis gave aryloxyamine 5 (96% yield), utilized as its HCl salt. A variation on this methodology was used to prepare oxime ethers derived from the equivalents of 2 and 4 (see below).

Figure 2:
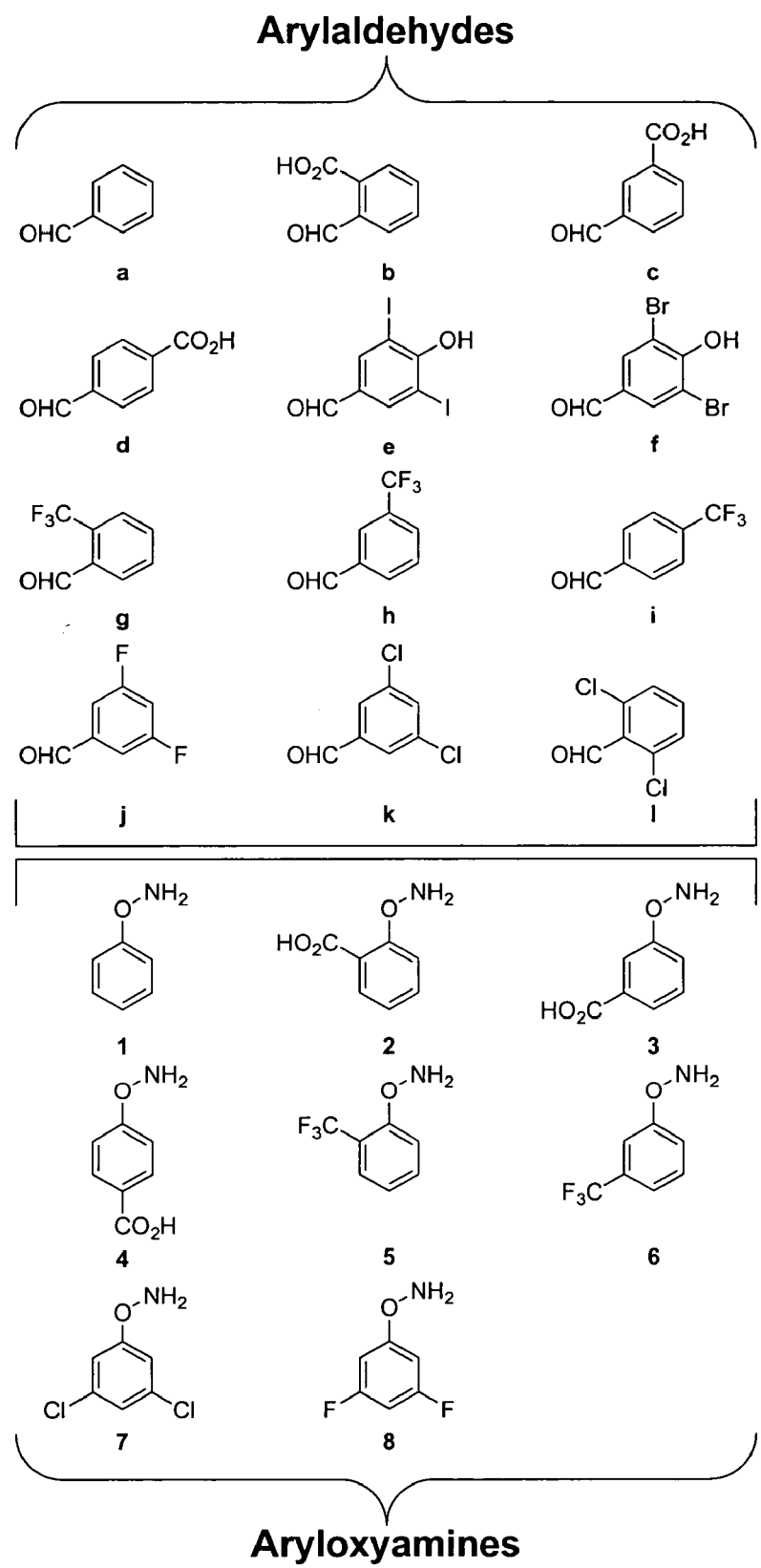
FIG. 2 illustrates the structures of aryloxyamine (1-8) and benzaldehyde (a-l) components used to synthesize the bisaryloxime ether library (see FIG. 1).

Aryloxyamines 1 and 5-8 were used to generate a portion of the oxime ether library (FIG. 2). Reactions between arylaldehydes (0.1 M) and aryloxyamines (0.125 M) in the presence of acetic acid (0.08 M) in DMSO afforded the oxime ethers in near quantitative yields within 24 h at 25° C. (all the phenoxyamines and hydrazines were tested as TTR amyloid inhibitors, owing to their use in excess in the library syntheses, revealing no inhibition). Five aryloxyamines (1 and 5-8) and twelve aldehydes (a-l) were condensed in all possible combinations to yield 60 oxime ethers using a Gilson 215 liquid handler in a single compound per well format. Reactions were analyzed by LC-MS to determine yield (98-100%, based on aldehyde consumption, see experimental) and product purity (>95%) in all wells, with all products displaying their expected masses. In the seven cases (1e, 5d-f, 7e, and 8e-f) where pure compounds were synthesized conventionally and complete characterization performed (see supporting information experimental), HPLC co-elution confirmed product structures and purity.

Figure 9:
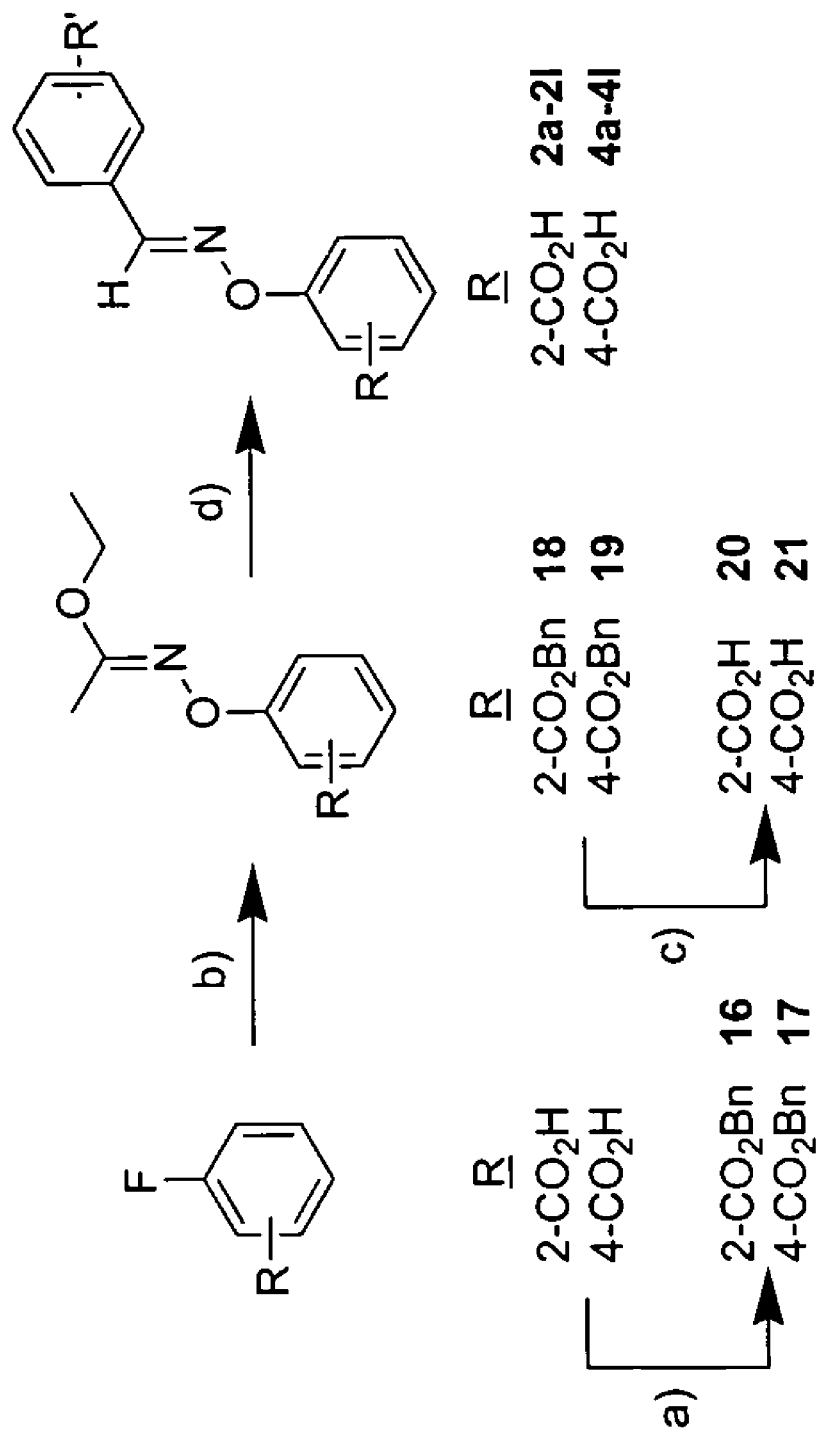
FIG. 9 illustrates a scheme showing the synthesis of bisaryloxime ethers by a trans-imination approach.

The remaining members of the oxime ether library were prepared by traditional synthetic procedures and isolated in mg quantities (see experimental and supporting information for complete characterization data and FIG. 8 for compound purity as determined by RP-HPLC). O-(3-Carboxyphenyl) hydroxylamine (3) was condensed with arylaldehydes a-l in the presence of catalytic HCl to afford oxime ethers 3a-l in moderate to excellent yields. Compounds 20 and 21 were prepared in 45 and 51% overall yields, respectively, using the ethyl-N-hydroxyacetimidate $S_NAr$ procedures (FIG. 9). The arylacetimidates were not hydrolyzed to the corresponding aryloxyamines 2 and 4, instead they were mixed with stoichiometric amounts of arylaldehydes under acidic conditions to afford oxime ethers 2a-l and 4a-l directly in moderate to excellent yields (oxime ether 2b was not isolable due to instability).

The inhibitory activity of the oxime ethers (7.2 µM) against acid-mediated (pH 4.4) TTR (3.6 µM) amyloid formation is summarized in FIG. 10. Of the 95 oxime ethers synthesized, 31 show good efficacy, reducing TTR amyloid formation to <10% of that exhibited by WT-TTR in the absence of inhibitor (90% inhibition, blue), 9 exhibit moderate activity (11-30% fibril formation, green), and the remaining 55 display poor activity (yellow).

Oxime ethers derived from benzaldehydes with a thyroxine-like substitution pattern (FIG. 10, rows e & f) are highly efficacious (all 16 displayed >90% inhibition), even when coupled with an unsubstituted phenoxyamine, a coupling that typically results in poor oxime ether inhibitors. These results challenge previous beliefs that appropriate substituents are required on both rings to achieve inhibition.

Additional oxime ethers resulting from the condensation of halogenated aryloxyamines with meta- or para-carboxybenzaldehydes or vice versa produced potent inhibitors, irrespective of which ring bears the carboxylic acid substituent. These results suggest that binding orientations may change to preserve electrostatic interactions with the $\epsilon$-$NH_3^+$ group of Lys-15. No oxime ethers derived from ortho-carboxybenzaldehyde produce good inhibitors. The activity of the carboxybenzaldehyde derived oxime ethers ranked from best to worst is meta>para>ortho, similar to that of oxime ethers derived from the carboxyphenoxyamines: meta≈para>ortho. Oxime ethers bearing carboxylic acids or halogens on both rings (excluding $T_4$-like substitution) displayed moderate activity at best.

Although the facility with which arylaldehydes and phenoxyamines condense lends itself to a dynamic combinatorial library approach (Nazarpack-Kandlousy, N.; et al. J. Comb. Chem. 1999, 199-206; Hochgürtel, M.; et al. Proc. Nat. Acad. Sci., U.S.A. 2002, 99, 3382-3387), a potential complication is a previous report that inhibition is typically maximal with two different small molecules bound owing to the allosteric communication between the two binding sites (Green, N. S.; et al. J. Am. Chem. Soc. 2003, 125, 13404-13414). Hence, the structure activity relationship data may be complicated by the influence of combinations of inhibitors produced in a dynamic combinatorial library.

Bisaryaldoxime Ether Stability. Although many bisaryaldoxime ethers are potent inhibitors of TTR amyloidogenesis (FIG. 10), they exhibit a range of stabilities in either acidic or basic aqueous media (first order degradation half-lives range from hours to days in the absence of TTR). While the oxime ethers, unlike the hydrazones, appear stable towards Schiff base hydrolysis in neutral and basic conditions, they can still slowly decompose with first order kinetics apparently by cleavage of their N—O bond to afford a phenol and an arylnitrile. This N—O bond cleavage, while precedented at higher temperatures, was not expected under such mild conditions (Miller, M. J.; Loudon, G. M. J. Org. Chem. 1975, 40,126-127; Supsana, P.; Tsouongas, P. G.; Varvounis, G. Tet. Lett. 2000, 41, 1845-1847; Knudsen, R. D.; Snyder, H. R. J. Org. Chem. 1974, 39, 3343-3346; Gómez, V.; Pérez-Medrano, A. J. Org. Chem. 1994, 59, 1219-1221; Cho, B. R.; et al. J. Org. Chem. 1991, 56, 5513-5517; Royer, R. E.; et al. J. Med. Chem. 1986, 29, 1799-1801; Castellino, A. J.; Rapoport, H. J. Org. Chem. 1986, 51, 1006-1011; Blake, J. A.; et al. J. Org. Chem. 2004, 69, 3112-3120).

The oxime ethers are qualitatively more stable than the analogous hydrazones according to their apparent degradation 'half-lives' (apparent hydrazone 'half-lives' refer to the time required for 50% disappearance, as the degradation process is not first order). Electron donating groups and ortho-substituents on either aromatic ring appear to increase the degradation rate of both the bisaryaldoxime ethers and bisarylhydrazones.

In general, inhibitor (7.2 µM) binding to TTR (3.6 µM) acts to stabilize the compounds from degradation under acid-mediated fibril formation conditions (pH 4.4, 37° C., 72 h). For 11 of the best inhibitors (<10% fibril formation), RP-HPLC analysis reveals that >74% of the initial oxime ether remains at the end of the acid-mediated fibril formation assay (FIG. 11). The least stable inhibitors (1e, 1f, 2k, 3g, 5d*) undergo nearly complete degradation in the absence of TTR within 72 h; however, its presence maintains >74% of the initial dose. Notably, inhibitor 5e exhibits no decomposition in the presence of TTR. This helps explain why many of the labile bisaryloxime inhibitors prove to be excellent inhibitors of TTR amyloidogenesis: not only do the inhibitors bind to TTR's thyroid hormone binding sites and impose kinetic stabilization on the TTR tetramer (Hammarström, P.; et al. *Science* 2003, 299, 713-716), but TTR binding also stabilizes the inhibitors against degradation.

Analyses were also performed to help confirm that the activities were primarily due to individual oxime ethers and not their proposed degradation products. To determine whether the degradative by-products contribute to the observed inhibitor efficacy, the corresponding phenols and nitriles (in the case of the oxime ethers), anilines (in the case of the hydrazones), and aldehydes (both oxime ethers and hydrazones) were analyzed for their fibril formation inhibition properties. The 3,5-dihalo-4-hydroxybenzonitrile and the analogous aldehyde degradation products are potent inhibitors of TTR fibril formation at concentrations twice that of tetrameric TTR (FIG. 12). 3,5-Dichlorophenol also inhibits fibril formation by 86% at concentration (7.2 µM), twice that of tetrameric TTR (3.6 µM). However, none of the other degradation products (nitriles, phenols, or anilines) display appreciable activity. It is therefore reasonable to conclude that the efficacy of the vast-majority of the amyloidogenesis inhibitors is due to the parent bisaryloxime ether and not the degradative by-products, providing the incentive to understand the mechanistic requirements for degradation and to stabilize these or related structures for medicinal chemistry purposes.

Analytical Ultracentrifugation Evaluation of TTR's Quaternary Structure Under Amyloidogenic Conditions in the Presence of Inhibitor 8f. Both sedimentation velocity and equilibrium analytical ultracentrifugation experiments were used to evaluate the influence of inhibitor 8f on TTR's quaternary structure under amyloidogenic conditions that typically dissociate the tetramer and make the monomer misassembly competent (72 h, pH 4.4, 37° C.). Oxime ether 8f (7.2 µM) bound to WT-TTR (3.6 µM) was subjected to sedimentation velocity analysis at 50,000 rpm (FIG. 13) under these conditions, revealing that TTR remains tetrameric, sedimenting as a single species with an S value of 3.7, corresponding to a molecular weight of 48.4±0.2 kDa. No tetrameric TTR was detectable in an identical experiment lacking inhibitor—only high molecular weight TTR aggregates were observed, consistent with the process of amyloidogenesis. Further scrutiny by sedimentation equilibrium analysis (17,000 rpm) reveal data that fit to a single ideal species model (FIG. 14; 52.1±0.2 kDa), in good agreement with the calculated molecular weight of tetrameric WT-TTR.(8f)$_2$ (56,374 Da). Analysis of the molecular weight distribution across the cell as a function of concentration also indicated a single species with a molecular weight slightly above 50 kDa.

Selectivity of Oxime Ether Binding to TTR in Human Blood Plasma. In order to employ small molecules in clinical studies to test the amyloid hypothesis (the idea that the process of amyloidogenesis leads to neurotoxicity or tissue damage), they must bind selectively to TTR in blood plasma in the presence of all other plasma proteins. The binding stoichiometry of the most active oxime ethers to TTR in human blood plasma was evaluated using an antibody capture/HPLC method reported previously (Purkey, H. E.; et al. *Proc. Natl. Acad. Sci. U.S.A* 2001, 98, 5566-5571). Briefly, the test compound is dissolved in human blood plasma at a concentration of 10.8 µM (approximately two to three times the plasma concentration of TTR). After incubation for 24 h (37° C.), TTR and any small molecules bound to it are immunoprecipitated using a polyclonal TTR antibody covalently linked to sepharose resin. The resin is washed, the TTR.(small molecule)$_{n<2}$ complex is dissociated at high pH, and the stoichiometry of small molecule bound to TTR is then determined by reverse phase analytical HPLC employing standard curves to quantify the relative amounts of inhibitor and TTR (maximum inhibitor stoichiometry is 2, owing to TTR's two thyroxine binding sites). This method establishes a lower limit for inhibitor binding stoichiometry because some of the inhibitor may be lost in the necessary wash steps following antibody capture.

The lower limits of the binding stoichiometry of bisaryloxime ethers displaying >90% amyloid inhibition (7.2 µM) to plasma TTR are presented in FIG. 15. Of the 31 compounds tested, 11 exhibit TTR binding stoichiometries exceeding 1.0, with three showing greater than 1.5 equivalents bound. Oxime ethers exhibiting the highest binding stoichiometry are derived from aldehydes where one aromatic ring bears a thyroxine-like (e.g. 3,5-dihalo-4-hydroxy) substitution pattern. This result is very important because it implies that incorporation of a 3,5-dihalo-4-hydroxy substituted aryl ring imparts TTR plasma binding selectivity over the majority of other plasma proteins including the thyroxine transport protein albumin, which has a concentration ~150 times greater than that of TTR (Stockigt, J. R. Thyroid Hormone Binding and Metabolism. *Endocrinology, Fourth Ed*. Degroot, L. J., Jameson, J. L., Eds.; W.B. Saunders Co.: Philadelphia, 2001, Volume 2, Chapter 94, 1314-1326; Petitpas, I.; et al. *Proc. Nat. Acad. Sci., U.S.A.* 2003, 100, 6440-6445). However, these results do not address the potential of these compounds to bind to the primary thyroxine transport protein in blood, TBG, which is at a concentration roughly ¹⁄₁₀ that of TTR. Hence, saturation of TBG's binding capacity would have little effect on the TTR binding selectivity results (Stockigt, J. R. Thyroid Hormone Binding and Metabolism. *Endocrinology, Fourth Ed*. Degroot, L. J., Jameson, J. L., Eds.; W.B. Saunders Co.: Philadelphia, 2001, Volume 2, Chapter 94, 1314-1326). Several of the oxime ethers synthesized via automated procedures displaying binding stoichiometries exceeding 0.5 (1e, 5d-f, 7e, and 8e-f) were also synthesized by conventional methods in mg quantities, isolated, and their binding stoichiometry re-evaluated. In all cases the same results were obtained, demonstrating that the oxime ethers prepared via automation and those prepared by conventional methods were identical.

Figure 16:
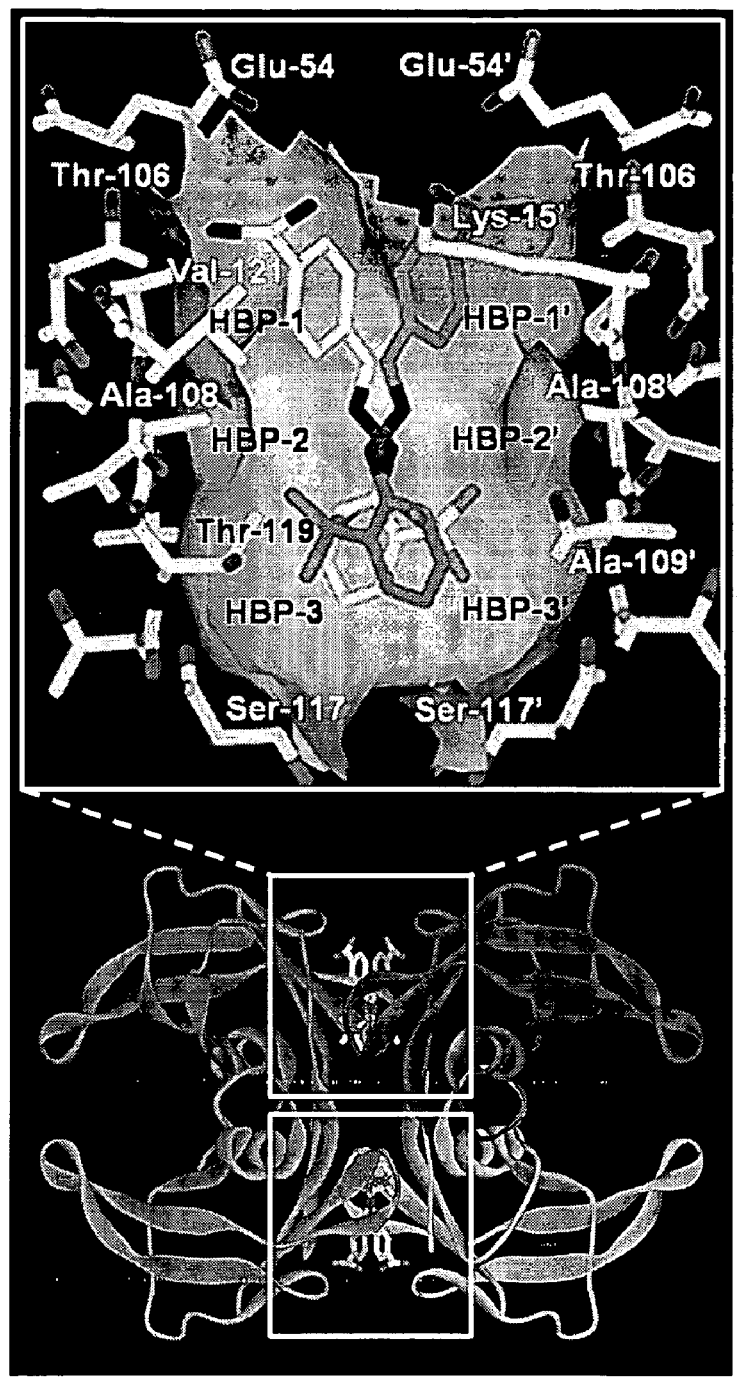
FIG. 16 illustrates a ribbon diagram depiction of bisaryloxime ether 5d bound to both of the WT-TTR thyroxine binding cavities (white boxes) based on X-ray crystallographic data.

Crystal Structure of WT-TTR.(5d)$_2$. To elucidate the structural basis for amyloid inhibition by the bisaryloxime ethers, the co-crystal structures of several compounds displaying both potent aggregation inhibition and plasma selectivity were undertaken. The WT-TTR.(5d)$_2$ complex provided the best co-crystal structure data, with 1.53 Å resolution, and is presented herein (FIG. 16 and FIG. 17). In spite of the high resolution data, the trifluoromethyl-substituted aromatic ring is visible only at less than 1σ contouring of the electron density omit maps, indicating relatively high flexibility in those regions. However, the side chain orientations and the shake 'n' warp omit maps (Reddy, V.; et al. *Acta Crystallogr., Sect. D, Biol. Crystallogr.* 2003, 59, 2200-2210) yielded the final orientation and position of two molecules bound within the protein's central channel (one in each thyroid hormone binding pocket), approximately in their minimum energy conformations. Each hormone site contains two symmetry equivalent binding conformations due to the 2-fold symmetry axis bisecting the binding channel.

Inhibitor 5d resides in TTR in a "forward" binding mode, which refers to those inhibitors having a carboxylic acid substituted aromatic ring placed in the outer cavity to make favorable electrostatic interactions with Lys-15 (Klabunde, T.; et al. *Nat. Struct. Biol.* 2000, 7, 312-321). The carboxyl group forms hydrogen bonds with the Thr-106 (2.73 Å) and Lys-15 residues; the Lys-15 side chain contributes to both hydrophobic ($\epsilon$-$CH_2$) and electrostatic ($\epsilon$-$NH_3^+$-3.3 Å) interactions with the inhibitor. Binding is also stabilized by both hydrophobic and van der Waals interactions, as the inhibitor is stacked between the hydrophobic side chains of Leu-17, Leu-17', Ala-108, Ala-108', Leu-110, Leu-110', Thr-119, Thr-119', Val-121, and Val-121'. The trifluoromethyl substituent occupies part of halogen binding pocket 3 (HBP-3) in the inner cavity. The inner cavity Ser-117 hydroxyl groups orient away from the inhibitor, contributing additional hydrophobic interactions via their $\beta$-$CH_2$ substructures. The linker oxygen and nitrogen do not appear to make electrostatic interactions with TTR and therefore may not contribute greatly to its binding and activity, consistent with the similar activities displayed by the oxime ethers and hydrazones and previous reports that stilbenes, diarylamines, and diaryl ethers are all active (Hammarström, P.; et al. *Science* 2003, 299, 713-716; Sacchettini, J. C.; Kelly, J. W. *Nat. Rev. Drug Disc.* 2002, 1, 267-275; Cohen, F. E.; Kelly, J. W. *Nature* 2003, 426, 6968, 905-909; Miller, S. R.; Sekijima, Y.; Kelly, J. W. *Lab. Invest.* 2004, 84, 545-552; Miroy, G. J.; et al. *Proc. Natl. Acad. Sci. U.S.A.* 1996, 93, 15051-15056; Peterson, S. A.; et al. *Proc. Natl. Acad. Sci. U.S.A.* 1998, 95, 12956-12960; Petrassi, H. M.; et al. *J. Am. Chem. Soc.* Submitted; Purkey, H. E.; et al. *Chemistry & Biology.* In press; Adamski-Werner, S. L.; et al. *J. Med. Chem.* 2004, 47, 355-374; Green, N. S.; et al. *J. Am. Chem. Soc.* 2003, 125, 13404-13414; Petrassi, H. M.; et al. *J. Am. Chem. Soc.* 2000, 122, 2178-2192; Baures, P. W.; et al. *Bioorg. Med. Chem.* 1998, 6, 1389-1401; Oza, V. B.; et al. *Bioorg. Med. Chem. Lett.* 1999, 9, 1-6; Baures, P. W.; et al. *Bioorg. Med. Chem.* 1999, 7, 1339-1347; Klabunde, T.; et al. *Nat. Struct. Biol.* 2000, 7, 312-321; Oza, V. B.; et al. *J. Med. Chem.* 2002, 45, 321-332; Razavi, H.; et al. *Angew. Chem. Int. Ed.* 2003, 42, 2758-2761). However, the conformation adopted by the linker appears to be crucial to orient the two aromatic rings.

Experimental:

General Synthetic Methods.

Unless otherwise stated, all chemicals were purchased from commercial suppliers and used without further purification. Reaction progress was monitored by thin-layer chromatography on silica gel 60 F254 coated glass plates (EM Sciences) and/or by analytical RP-HPLC. All flash chromatography was performed using 230-400 mesh silica gel 60 (EM Sciences). NMR spectra were recorded on either Bruker 300, 400, 500, or 600 MHz spectrometers. Chemical shifts are reported in parts per million downfield from the internal standard $Me_4Si$ (0.0 ppm) for $CDCl_3$ solutions, or in the case where the $Me_4Si$ was not seen in the $^{13}C$-NMR spectra, calibration was done on the solvent peaks ($CDCl_3$ 77.16 ppm). For samples in $d_6$-DMSO, $d_6$-Acetone, or $CD_3OD$, calibration was done on the solvent peak at 3.49, 2.05, and 3.31 ppm respectively for $^1H$-NMR and 39.52, 29.84, and 49.00 ppm respectively for $^{13}C$-NMR. Reverse phase high performance liquid chromatography (RP-HPLC) was carried out on a Waters 600 E multi-solvent delivery system employing a Waters 486 tunable absorbance detector and a Waters 717 autosampler. A ThermoHypersil-Keystone Betabasic-18 column was used for analytical reverse phase HPLC analyses (model 71503-034630, 150 Å pore size, 3 μm particle size) and a Vydac C18 column for preparative HPLC (model 218TP1022, 300 Å pore size, 5 μm particle size, 22 mm i.d. by 250 mm). Solvent system A was 95:5 $H_2O$:$CH_3CN$ with 0.25% trifluoroacetic acid (TFA) and solvent B was 5:95 $H_2O$:$CH_3CN$ with 0.25% TFA: linear gradients were run from either 0:100, 80:20, or 60:40 A:B to 0:100 A:B. High performance liquid chromatography mass spectrometry (HPLC-MS) was performed on a Hewlett Packard HPLC-MS equipped with a Zorbax SB-C18 (5 mm, 2.1×50 mm) column: solvent delivery was performed using a Gilson 215 liquid handler. All mass spectrometry data were collected at the Scripps Research Institute Center for Mass Spectrometry.

Representative Procedure for the Copper Mediated Coupling of Phenylboronic Acids and N-Hydroxyphthalimide for the Preparation of Phenoxyamines (Method 1): Synthesis of 9

A 20 mL scintillation vial was charged with N-hydroxyphthalimide (163 mg, 1.0 mmol), copper (I) chloride (99 mg, 1.0 mmol), freshly activated 4 Å molecular sieves (~250 mg), and phenylboronic acid (244 mg, 2.0 mmol). 1,2-Dichloroethane (5 mL) was added followed by pyridine (90 μL, 1.1 mmol), resulting in a light brown suspension. The cap was loosely applied such that the reaction suspension was open to air and stirred at room temperature until completion as detected by analytical RP-HPLC (mixture color turned from brown to emerald green as the reaction proceeded). Upon completion (~48 h), the mixture was adsorbed onto silica gel and concentrated to a powder. Flash chromatographic purification over silica (25% EtOAc in hexanes) afforded N-phenoxyphthalimide 9 as a white solid (216 mg, 90%); see below for characterization data.

N-Phenoxyphthalimide (9)

Preparation of 9 was described above as the representative procedure (method 1). $^1H$-NMR (500 MHz, $CDCl_3$) δ 7.12-7.20 (m, 3H), 7.32-7.38 (m, 2H), 7.80-7.84 (m, 2H), 7.90-7.94 (m, 2H); $^{13}C$-NMR (125 MHz, $CDCl_3$) δ 114.4, 124.0, 128.8, 129.7, 134.9, 158.9, 162.9; MALDI-FTMS (DHB) 240.0656 m/z $[MH]^+$, $C_{14}H_{10}NO_3$, requires 240.0655.

N-(3-Trifluoromethylphenoxy)phthalimide (10)

3-Trifluoromethylphenylboronic acid (380 mg, 2.0 mmol) was subjected to the representative coupling procedure with N-hydroxyphthalimide (NHP) as outlined above (method 1). Flash chromatographic purification over silica (40% EtOAc in hexanes) afforded 10 as a white solid (270 mg, 88%). $^1H$-NMR (500 MHz, $CDCl_3$) δ 7.34-7.38 (m, 1H), 7.40-7.45 (m, 2H), 7.47 (m, J=0.9, 8.1 Hz, 1H), 7.82-7.87 (m, 2H), 7.92-7.97 (m, 2H); $^{13}C$-NMR (125 MHz, $CDCl_3$) δ 111.6, 117.8, 118.1, 121.4, 122.3, 124.2, 128.8, 130.5, 132.2, 135.1, 159.0, 162.8; LC-MS 309 m/z $[MH]^+$, $C_{15}H_9F_3NO_3$ requires 309.

N-(3,5-Dichlorophenoxy)phthalimide (11)

3,5-dichlorophenylboronic acid (382 mg, 2.0 mmol) was subjected to the representative coupling procedure with NHP as outlined above (method 1). Flash chromatographic purification over silica (50% $CH_2Cl_2$ in hexanes) afforded 11 as a white solid (139 mg, 45%). $^1$H-NMR (600 MHz, $CDCl_3$) δ 7.07 (m, 2H), 7.13-7.16 (m, 1H), 7.81-7.86 (m, 2H), 7.71-7.96 (m, 2H); $^{13}$C-NMR (150 MHz, $CDCl_3$) δ 113.7, 124.2, 125.0, 128.8, 135.2, 135.9, 159.7, 162.5; LC-MS 276 m/z $[MH]^+$, $C_{14}H_8Cl_2NO_3$ requires 276.

N-(3,5-Difluorophenoxy)phthalimide (12)

3,5-Difluorophenylboronic acid (316 mg, 2.0 mmol) was subjected to the representative coupling procedure with NHP as outlined above (method 1). Flash chromatographic purification over silica (10% $CH_2Cl_2$ in toluene) afforded 12 as a white solid (197 mg, 72%). $^1$H-NMR (600 MHz, $CDCl_3$) δ 6.58-6.63 (m, 1H), 6.68-6.73 (m, 2H), 7.82-7.87 (m, 2H), 7.92-7.97 (m, 2H); $^{13}$C-NMR (150 MHz, $CDCl_3$) δ 98.5 (m), 100.3 (t, $J_{C-F}$=25.3 Hz), 124.4, 128.7, 135.4, 160.5 (t, $J_{C-F}$=13.8 Hz), 162.6, 163.6 (dd, $J_{C-F}$=13.8, 249 Hz); MALDI-FTMS (DHB) 276.0456 m/z $[MH]^+$, $C_{14}H_8F_2NO_3$ requires 276.0467.

N-(3-Methoxycarbonylphenoxy)phthalimide (13)

3-Methoxycarbonylphenylboronic acid was subjected to similar coupling procedures with NHP as outlined above (method 1). A 100 mL round bottom flask was charged with N-hydroxyphthalimide (2.19 g, 13.4 mmol), copper (I) chloride (1.34 g, 13.5 mmol), freshly activated 4 Å molecular sieves (~5 g), and 3-methoxycarbonylphenylboronic acid (4.79 g, 26.6 mmol). 1,2-Dichloroethane (60 mL) was added followed by pyridine (1.20 mL, 14.8 mmol), and the reaction suspension was stirred in an air atmosphere at room temperature. After 4 days, the mixture was adsorbed onto silica gel and concentrated to a powder. Flash chromatographic purification over silica (33-50% gradient EtOAc in hexanes) afforded 13 as a white solid (1.85 g, 46%). $^1$H-NMR (500 MHz, $CDCl_3$) δ 3.90 (s, 3H), 7.38-7.41 (ddd, J=1.0, 2.5, 8.3 Hz, 1H), 7.44 (t, J=8.3 Hz, 1H), 7.78 (dd, J=1.0, 2.5 Hz, 1H), 7.82-7.86 (m, 3H), 7.92-7.96 (m, 2H); $^{13}$C-NMR (125 MHz, $CDCl_3$) δ 52.5, 115.0, 119.3, 124.3, 125.9, 129.0, 130.0, 132.1, 135.2, 159.0, 163.0, 166.2; ESI-MS 298 m/z $[MH]^+$, $C_{16}H_{12}NO_5$ requires 298.

Representative Procedure for the Hydrazinolysis of N-Aryloxyphthalimides to Corresponding O-Arylhydroxylamines (Method 1A): Synthesis of Compound 1

Hydrazine monohydrate (0.401 mL, 8.2 mmol) was added slowly to a solution of N-phenoxyphthalimide 9 (652 mg, 2.73 mmol) in 10% MeOH in $CHCl_3$ (25 mL) and the reaction was stirred at room temperature. Upon completion (TLC monitoring, 12 h) a white precipitate appeared (the phthalizine) in a colorless reaction solution. The reaction mixture was passed through a plug of silica gel, washing with 30% EtOAc in hexane. Removal of the EtOAc/hexanes produced a slightly pale yellow oil, which upon Kugelrohr distillation from $K_2CO_3$ (<10 mg) provided pure phenoxyamine 1 as a clear, colorless oil (238 mg, 80%); see below for characterization data. Alternatively, after removal of the EtOAc/hexanes, the yellow oil was dissolved in $Et_2O$ and cooled to 0° C. After 10 min at 0° C., 4 N HCl in dioxane was added dropwise until pH 3 was reached. The resulting white solid was filtered and washed with $Et_2O$ (2×10 mL) to afford 1 as the pure HCl salt (306 mg, 77%).

O-Phenylhydroxyamine hydrochloride (1)

Preparation of 1 was described above as the representative procedure (method 1A). $^1$H-NMR (400 MHz, $CD_3OD$) δ 6.84-6.89 (m, 1H), 7.03-7.09 (m, 2H), 7.19-7.25 (m, 2H); $^{13}$C-NMR (100 MHz, $CD_3OD$) δ 114.1, 121.6, 130.3, 163.1; LC-MS 110 m/z $[MH]^+$, $C_6H_8NO$ requires 110.

O-(3-Trifluoromethylphenyl)hydroxylamine (6)

N-(3-Trifluoromethylphenoxy)phthalimide 10 (1.12 g, 3.65 mmol) was subjected to the representative hydrazinolysis reaction as described above (method 1A). Distillation (85° C./6 mm) provided pure 6 as a clear colorless liquid (582 mg, 90%). $^1$H-NMR (500 MHz, $CDCl_3$) δ 6.00 (s, 2H), 7.19-7.21 (m, 1H), 7.30 (dd, J=8.4, 2.6 Hz, 1H), 7.38 (t, J=8.1 Hz, 1H), 7.45-7.47 (m, 1H); $^{13}$C-NMR (125 MHz, $CDCl_3$) δ 110.4, 117.2, 117.9, 130.9, 162.1; LC-MS 178 m/z $[MH]^+$, $C_7H_7F_3NO$ requires 178.

O-(3,5-Dichlorophenyl)hydroxylamine (7)

N-(3,5-Dichlorophenoxy)phthalimide 11 (711 mg, 2.31 mmol) was subjected to the representative hydrazinolysis reaction as described above (method 1A). Elution of the reaction mixture through the silica gel plug resulted in solidification of free base 7 as a white solid (378 mg, 92%). $^1$H-NMR (600 MHz, $CDCl_3$) δ 5.91 (s, 2H), 6.91-6.93 (m, 1H). 7.06-7.09 (m, 2H); $^{13}$C-NMR (150 MHz, $CDCl_3$) δ 112.9, 121.9, 135.9, 163.2; LC-MS 179 m/z $[MH]^+$, $C_6H_6Cl_2NO$ requires 179.

O-(3,5-Diflourophenyl)hydroxylamine hydrochloride (8)

N-(3,5-Difluorophenoxy)phthalimide 12 (1.74 g, 6.31 mmol) was subjected to the representative hydrazinolysis reaction as described above (method 1A). Precipitation of the HCl salt afforded 8 as a white solid (980 mg, 86%). $^1$H-NMR (600 MHz, $CD_3OD$) δ 6.83-6.90 (m, 3H); $^{13}$C-NMR (150 MHz, $CD_3OD$) δ 99.3 (dd, $J_{C-F}$=8.0, 24.9 Hz), 101.1 (t, $J_{C-F}$=26.4 Hz), 160.0, 165.8 (dd, $J_{C-F}$=15, 248 Hz); LC-MS 146 m/z $[MH]^+$, $C_6H_6F_2NO$ requires 146.

O-(3-Methoxycarbonylphenyl)hydroxylamine (14)

N-(3-Methoxycarbonylphenoxy)phthalimide 13 (271 mg, 0.912 mmol) was subjected to the representative hydrazinolysis reaction as described above (method 1A) to afford 14 as a pale yellow syrup (146 mg, 96%). $^1$H-NMR (500 MHz, $CDCl_3$) δ 3.91 (s, 3H), 5.92 (s, 2H), 7.29-7.32 (m, 1H), 7.33 (t, J=6.9 Hz, 1H), 7.63 (dt, J=1.8, 6.9 Hz, 1H), 7.82-7.84 (m, 1H); $^{13}$C-NMR (125 MHz, $CDCl_3$) δ 52.3, 114.2, 118.1, 122.5, 129.3, 131.4, 161.4, 167.1; GC-MS 167 m/z $[M]^+$, $C_8H_9NO_3$ requires 167, 152 m/z $[M-NH]^+$, $C_8H_8O_3$ requires 152.

O-(3-Carboxyphenyl)hydroxylamine (3)

$LiOH \cdot H_2O$ (91.0 mg, 2.17 mmol) was added to a solution of O-(3-methoxycarbonyl-phenyl)hydroxylamine 14 (90.4 mg, 0.541 mmol) in a 3/1/1 mL mixture of $THF/MeOH/H_2O$ and the reaction was stirred at room temperature. After 24 h the reaction was diluted with H$_2$O (50 mL), acidified to pH-3-4 with 0.5 N HCl, and extracted with EtOAc (3×25 mL). The combined organics were washed with H$_2$O (25 mL) and brine (25 mL), dried over Na$_2$SO$_4$, filtered, and concentrated to afford 3 as a white solid (78.7 mg, 95%). $^1$H-NMR (500 MHz, d$_6$-DMSO) δ 7.01 (s, 2H), 7.24 (ddd, J=1.4, 2.8, 8.3 Hz, 1H), 7.34 (t, J=7.8 Hz, 1H), 7.46 (dt, J=1.4, 7.3 Hz, 1H), 7.68 (dd, J=1.4, 2.8 Hz, 1H); $^{13}$C-NMR (125 MHz, d$_6$-DMSO) δ 113.5, 117.8, 121.3, 129.2, 131.8, 161.7, 167.3; ESI-MS 162 m/z [M-H$^+$]$^-$, C$_7$H$_6$NO$_3$ requires 162.

Ethyl-N-(2-trifluoromethylphenoxy)acetimidate (15)

Prepared using a procedure adapted from Miyazawa et al. (Miyazawa, E.; et al. Org. Prep. Proced. Int. 1997, 29, 594-600) $^t$BuOK (0.78 g, 6.7 mmol) was added to a stirring solution of ethyl-N-hydroxyacetimidate (1.00 g, 6.06 mmol) in anhydrous DMF (6 mL) at 0° C. under an Ar atmosphere. After $^t$BuOK addition was completed the reaction was stirred at room temperature. After 30 min 2-fluorobenzotrifluoride (1.29 mL, 6.06 mmol) was added and the reaction was heated at 80° C. for 2 h. Upon cooling the reaction mixture was diluted with ice water (100 mL) and extracted with EtOAc (3×40 mL). The combined organic layers were washed with brine (2×50 mL), dried with MgSO$_4$, and concentrated to afford a dark oil. Flash chromatographic purification over silica (10% EtOAc in hexanes) afforded 15 as a clear liquid (1.33 g, 89%). $^1$H-NMR (500 MHz, CDCl$_3$) δ 1.36 (t, J=7.1 Hz, 3H), 2.15 (s, 3H), 4.20 (q, J=7.1 Hz, 2H), 6.99 (apparent t, J=7.5 Hz, 1H), 7.47 (apparent dt, J=7.9 Hz, 1H), 7.52-7.57 (m, 2H); $^{13}$C-NMR (125 MHz, CDCl$_3$) δ 14.3, 14.5, 63.2, 114.2, 116.2 (q, J$_{C-F}$=31 Hz), 120.3, 123.7 (q, J$_{C-F}$=272 Hz), 126.4 (q, J$_{C-F}$=4.8 Hz), 133.2, 157.2 (q, J$_{C-F}$=1.9 Hz), 167.1; LC-MS 248 m/z[MH]$^+$, C$_{11}$H$_{13}$F$_3$NO$_2$ requires 248.

O-(2-Trifluoromethylphenyl)hydroxylamine hydrochloride (5)

Prepared using a procedure adapted from Miyazawa et al., (Miyazawa, E.; et al. Org. Prep. Proced. Int. 1997, 29, 594-600) 70% HClO$_4$ (12 mL) was added dropwise to a solution of 15 (4.14 g, 16.7 mmol) in 1,4-dioxane (19 mL) at 0° C., then the reaction was stirred at room temperature overnight. The reaction mixture was then poured into ice water (150 mL) and adjusted to pH 13 with solid NaOH pellets. The aqueous layer was extracted with EtOAc (3×150 mL) and the combined organics were washed with brine (2×75 mL), dried over MgSO$_4$, and concentrated to afford a dark residue. Flash chromatographic purification over silica (15% EtOAc in hexanes) followed by precipitation of the HCl salt, as described above for other aryloxyamines, afforded 5 as a white solid (3.42 g, 96%). $^1$H-NMR (600 MHz, CD$_3$OD) δ 7.37-7.41 (m, 1H), 7.48-7.51 (m, 1H), 7.76-7.79 (m, 2H); $^{13}$C-NMR (150 MHz, CD$_3$OD) δ 114.6, 125.0, 126.3, 127.6 (q, J$_{C-F}$=5.7 Hz), 128.3 134.5; LC-MS 178 m/z [MH]$^+$, C$_7$H$_7$F$_3$NO requires 178.

Library Synthesis for Aryloxyamine 1 & 5-8 Based Oxime Ethers

Libraries were prepared in a single compound per well format. Stock solutions of all aldehydes (0.5 M) and aryloxyamines (0.4 M) were prepared in DMSO. A Gilson 215 Liquid Handler equipped with a 1 mL syringe, 1.1 mL tubing, and a 13 mm I.D. probe was used to distribute all solutions into a 96 well (2 mL volume) polypropylene plate at a rate of 0.3 mL/min. To make 0.5 mL of a 0.1 M solution of each oxime ether, 100 μL (0.05 mmol, 1 eq.) of aldehyde, 156 μL (0.63 mmol, 1.25 eq.) of aryloxyamine, and 244 μL of 0.164 M acetic acid, were distributed to each well of the plate. The plate was covered and agitated for 24 h at room temperature using a dual action shaker. The reactions were diluted to 720 μM in DMSO and analyzed by LC-MS to determine yield, purity, and identity. Compounds were stored frozen at −20° C. after synthesis.

Reaction yield was determined using the integrated value of aldehyde that remained in the reaction mixture. Calibration curves of all aldehydes were made and the yield of each oxime ether was calculated assuming all the aldehyde that reacted quantitatively formed oxime ether; i.e. if 5% of aldehyde remained in the reaction mixture the yield of oxime ether would be 95%. Yields ranged from 98-100% and >95% purity in all wells.

Representative Procedure for the Coupling of O-(3-Carboxyphenyl)hydroxylamine 3 to Arylaldehydes a-l (Method 2)

To a stirring solution of O-(3-carboxyphenyl)hydroxylamine 3 (~0.2 mmol, 1 eq.) in 1,4-dioxane (3.0 mL) was added the aldehyde (1 eq.) followed by 1 drop of 0.5 N HCl, then the reaction was stirred at room temperature. Upon completion as determined by reverse phase HPLC (3-18 h), the reaction was diluted with H$_2$O (15 mL) and the precipitate filtered, washed with H$_2$O, collected, and dried in vacuo. Refer to the supporting information for specific synthetic details and characterization data for inhibitors 3b-l analogous to that reported for 3a below.

Benzaldehyde-O-(3-carboxyphenyl)oxime (3a)

Benzaldehyde (21.0 μL, 0.207 mmol) was subjected to the representative coupling procedure with 3 (31.8 mg, 0.208 mmol) as outlined above (method 2), yielding 3a as a white solid (29.0 mg, 58%). $^1$H-NMR (500 MHz, 1:1 CD$_3$OD:d$_6$-DMSO) δ 7.39-7.45 (m, 5H), 7.59-7.64 (m, 1H), 7.71-7.78 (m, 3H), 8.58 (s, 1H); $^{13}$C-NMR (125 MHz, d$_6$-DMSO) δ 114.5, 118.8, 123.3, 127.7, 129.1, 129.3, 130.8, 131.1, 132.3, 153.3, 158.9, 166.9; MALDI-FTMS (DHB) 242.0812 m/z [MH]$^+$, C$_{14}$H$_{12}$NO$_3$ requires 242.0812. RP-HPLC: 98% pure.

Benzyl-2-fluorobenzoate (16)

Benzyl alcohol (2.60 mL, 25.1 mmol) was added slowly to a stirring solution of 2-fluorobenzoic acid (2.92 g, 20.8 mmol), 4-(dimethylamino)pyridine (251 mg, 2.05 mmol), and 1,3-dicyclohexylcarbodiimide (5.16 g, 25.0 mmol) in anhydrous CH$_2$Cl$_2$ at room temperature under an Ar atmosphere. After 18 h the precipitate was filtered off and washed with CH$_2$Cl$_2$, and the filtrate was concentrated with silica to a powder. Flash chromatographic purification over silica (10% to 20% gradient EtOAc in hexanes) afforded 16 as a clear, colorless liquid (4.20 g, 88%). $^1$H-NMR (500 MHz, CDCl$_3$) δ 5.39 (s, 2H), 7.14 (ddd, J=1.1, 8.4, 9.5 Hz, 1H), 7.20 (dt, J=1.1, 7.7 Hz, 1H), 7.31-7.36 (m, 1H), 7.37-7.41 (m, 2H), 7.44-7.48 (m, 2H), 7.49-7.55 (m, 1H), 7.96 (dt, J=1.8, 7.3 Hz); $^{13}$C-NMR (125 MHz, CDCl$_3$) δ 66.93, 117.0 (d, J$_{C-F}$=22.1 Hz), 118.7 (d, J$_{C-F}$=9.6 Hz), 124.0 (d, J$_{C-F}$=3.8 Hz), 128.1, 128.2, 128.6, 132.2, 134.6 (d, J$_{C-F}$=9.6 Hz), 135.7, 162.1 (d, J$_{C-F}$=260 Hz), 164.2 (d, J$_{C-F}$=3.8 Hz); GC-MS 230 m/z [M]+, C$_{14}$H$_{11}$OF$_2$ requires 230.

Benzyl-4-fluorobenzoate (17)

Benzyl alcohol (4.05 mL, 39.1 mmol) was added slowly to a stirring solution of 4-fluorobenzoic acid (5.00 g, 35.7 mmol), 4-(dimethylamino)pyridine (432 mg, 3.53 mmol), and 1,3-dicyclohexylcarbodiimide (8.15 g, 39.5 mmol) in anhydrous $CH_2Cl_2$ at room temperature under an argon atmosphere. After 18 h the reaction was worked up according to procedures as outlined for the synthesis of 16. Flash chromatographic purification over silica (10% EtOAc in hexanes) afforded 17 as a clear, colorless liquid (7.75 g, 94%). $^1$H-NMR (500 MHz, $CDCl_3$) δ 5.35 (s, 2H), 7.06-14 (m, 2H), 7.32-7.41 (m, 3H), 7.41-7.47 (m, 2H), 8.06-8.12 (m, 2H); $^{13}$C-NMR (125 MHz, $CDCl_3$) δ 66.84, 115.5 (d, $J_{C-F}$=22.0 Hz), 126.4 (d, $J_{C-F}$=2.9 Hz), 128.2, 128.3, 128.6, 132.3 (d, $J_{C-F}$=9.6 Hz), 135.9, 165.5, 165.8 (d, $J_{C-F}$=253 Hz); GC-MS 230 m/z [M]+, $C_{14}H_{11}OF_2$ requires 230.

Ethyl-N-(2-benzyloxycarbonylphenoxy)acetimidate (18)

To a stirring solution of ethyl-N-hydroxyacetimidate (2.06 g, 20.0 mmol) in anhydrous DMF (60 mL) under Ar was added $^t$BuOK (2.21 g, 19.7 mmol) all at once. After 30 min benzyl-2-fluorobenzoate 16 (4.13 g, 17.9 mmol) was added as a solution in DMF (20 mL) and the reaction was stirred at room temperature. After 3 h the reaction was diluted with $H_2O$ (400 mL), extracted with EtOAc (3×100 mL), and the combined organics were washed with $H_2O$ (3×50 mL) and brine (50 mL), dried over $Na_2SO_4$, filtered, and concentrated. Flash chromatographic purification over silica (5-10% gradient EtOAc in hexanes) afforded 18 as a clear syrup (3.61 g, 64%). $^1$H-NMR (500 MHz, $CDCl_3$) δ 1.34 (t, J=7.0 Hz, 3H), 2.00 (s, 3H), 4.18 (q, J=7.0 Hz, 2H), 5.34 (s, 2H), 6.96 (dt, J=1.1, 7.7 Hz, 1H), 7.30-7.35 (m, 1H), 7.35-7.39 (m, 2H), 7.42-7.48 (m, 3H), 7.55 (dd, J=1.1, 8.4 Hz, 1H), 7.90 (dd, J=1.8, 7.7 Hz, 1H); $^{13}$C-NMR (125 MHz, $CDCl_3$) δ 14.4, 14.5, 63.1, 66.6, 114.5, 117.0, 120.4, 128.2, 128.4, 128.5, 131.7, 133.8, 136.1, 159.5, 165.8, 166.7; GC-MS 313 m/z[M]+, $C_{18}H_{19}NO_4$ requires 313, 228 m/z [M-85]+, benzyl-2-hydroxybenzoate $C_{14}H_{12}O_3$ requires 228.

Ethyl-N-(4-benzyloxycarbonylphenoxy)acetimidate (19)

To a stirring solution of ethyl-N-hydroxyacetimidate (3.79 g, 36.8 mmol) in anhydrous DMF (150 mL) under Ar was added $^t$BuOK (4.09 g, 36.4 mmol) all at once. After 40 min benzyl-4-fluorobenzoate 17 (7.63 g, 17.9 mmol) was added and the reaction was stirred at room temperature. After 4 h the reaction was diluted with $H_2O$ (500 mL), extracted with EtOAc (4×100 mL), and the combined organics were washed with $H_2O$ (2×100 mL), dried over $Na_2SO_4$, filtered, and concentrated. Flash chromatographic purification over silica (5-10% gradient EtOAc in hexanes) afforded 19 as a clear syrup (6.02 g, 58%). $^1$H-NMR (500 MHz, $CDCl_3$) δ 1.36 (t, J=7.0 Hz, 3H), 2.12 (s, 3H), 4.20 (q, J=7.0 Hz, 2H), 5.34 (s, 2H), 7.15-7.19 (m, 2H), 7.31-7.35 (m, 2H), 7.36-7.41 (m, 2H), 7.42-7.36 (m, 2H), 8.00-8.14 (m, 2H); $^{13}$C-NMR (125 MHz, $CDCl_3$) δ 14.3, 14.4, 63.1, 66.4, 113.4, 122.9, 128.1, 128.1, 128.6, 131.5, 136.3, 163.5, 166.3, 166.4; GC-MS 228 m/z [M-85]+, benzyl-4-hydroxybenzoate $C_{14}H_{12}O_3$ requires 228.

Ethyl-N-(2-carboxyphenoxy)acetimidate (20)

$LiOH \cdot H_2O$ (431 mg, 10.3 mmol) was added to a solution of ethyl-N-(2-benzyloxycarbonylphenoxy)acetimidate 18 (802 mg, 2.56 mmol) in a 9/3/3 mL mixture of THF/MeOH/$H_2O$ and the reaction was stirred at room temperature. After 6 h the reaction was diluted with $H_2O$ (100 mL), washed with $CH_2Cl_2$ (4×30 mL), acidified to pH~5.0-5.5 with 0.5 N HCl, and extracted with EtOAc (4×30 mL). The combined organics were washed with $H_2O$ (30 mL) and brine (30 mL), dried over $Na_2SO_4$, filtered, and concentrated to afford 20 as a white solid (459 mg, 80%). $^1$H-NMR (500 MHz, $d_6$-Acetone) δ 1.34 (t, J=6.9 Hz, 3H), 2.18 (s, 3H), 4.20 (q, J=6.9 Hz, 2H), 7.02 (ddd, J=0.9, 7.3, 7.8 Hz, 1H), 7.51 (ddd, J=1.8, 7.3, 8.7 Hz, 1H), 7.60 (dd, J=0.9, 8.7 Hz, 1H) 7.86 (dd, J=1.8, 7.8 Hz, 1H); $^{13}$C-NMR (125 MHz, $d_6$-Acetone) δ 14.6, 14.7, 63.8, 115.2, 118.5, 121.3, 132.4, 134.5, 160.2, 166.8, 167.4; ESI-MS 224 m/z [MH]+, $C_{11}H_{14}NO_4$ requires 224.

Ethyl-N-(4-carboxyphenoxy)acetimidate (21)

$LiOH \cdot H_2O$ (550 mg, 13.1 mmol) was added to a solution of ethyl-N-(4-benzyloxycarbonylphenoxy)acetimidate 19 (1.04 g, 3.32 mmol) in a 9/3/3 mL mixture of THF/MeOH/$H_2O$ and the reaction was stirred at room temperature. After 24 h the reaction was diluted with $H_2O$ (100 mL), washed with $CH_2Cl_2$ (4×30 mL), acidified to pH~5.0-5.5 with 0.5 N HCl, and extracted with EtOAc (3×30 mL). The combined organics were washed with $H_2O$ (30 mL) and brine (30 mL), dried over $Na_2SO_4$, filtered, and concentrated to afford 21 as a white crystalline solid (698 mg, 94%). $^1$H-NMR (500 MHz, $CDCl_3$) δ 1.37 (t, J=6.9 Hz, 3H), 2.14 (s, 3H), 4.22 (q, J=6.9 Hz, 2H), 7.18-7.22 (m, 2H), 8.04-8.08 (m, 2H); $^{13}$C-NMR (125 MHz, $CDCl_3$) δ 14.5, 14.6, 63.3, 113.7, 122.1, 132.3, 164.2, 166.7, 172.0; ESI-MS 224 m/z [MH]+, $C_{11}H_{14}NO_4$ requires 224.

Representative Procedure for the Coupling of Ethyl-N-(2-carboxyphenoxy)-acetimidate 20 or Ethyl-N-(4-carboxyphenoxy)acetimidate 21 to Arylaldehydes a-l Yielding Oxime Ethers 2a-l and 4a-l, Respectively (Method 3)

To a solution of acetimidate 20 or 21 (~0.1-0.3 mmol, 1 eq.) and aldehyde (~0.1-0.3 mmol, 1 eq.) in 1,4-dioxane (2.0 mL) was added 70% $HClO_4$ (0.9 eq.) and the reaction was stirred at room temperature. Upon completion as determined by reverse phase HPLC (2-6 h), the reaction was diluted with $H_2O$ (20 mL) and the precipitate filtered, washed with $H_2O$, collected, and dried in vacuo. Refer to the supporting information for specific synthetic details and characterization data of inhibitors 2c-l and 4b-l analogous to 2a as shown below.

Benzaldehyde-O-(2-carboxyphenyl)oxime (2a)

70% $HClO_4$ (14.0 μL, 0.163 mmol), benzaldehyde (18.0 mL, 0.177 mmol), and 20 (39.0 mg, 0.175 mmol) were subjected to the representative coupling procedure as outlined above (method 3), yielding 2a as a white solid (26.1 mg, 62%). $^1$H-NMR (500 MHz, $d_6$-Acetone) δ 7.15 (dt, J=0.9, 7.8 Hz, 1H), 7.48-7.55 (m, 3H), 7.59 (dt, J=1.8, 7.8 Hz, 1H), 7.71 (d, J=8.2 Hz, 1H), 7.83-7.89 (m, 3H), 8.66 (s, 1H), 10.8-11.5 (broad s, 1H); $^{13}$C-NMR (125 MHz, $d_6$-DMSO) δ 115.7, 119.7, 122.1, 127.8, 129.0, 130.8, 130.9, 131.1, 133.1, 153.4, 157.7, 166.8; MALDI-FTMS (DHB) 242.0811 m/z [MH]+, $C_{14}H_{12}NO_3$ requires 242.0812. RP-HPLC: >99% pure.

Fibril Formation Assay

Wild type TTR was purified from an *Escherichia coli* expression system as described previously (Lashuel, H. A.; et al. *Biochemistry* 1999, 38, 13560-13573). Disposable cuvettes (Fisher #14 385 938) were charged with 495 µL of a 0.4 mg/mL stock of TTR (7.2 µM) in 10 mM phosphate (pH 7.2), 100 mM KCl, 1 mM EDTA, and 0.2% $NaN_3$. 5 µL of the inhibitors in DMSO (1.44 mM) were added to the TTR solutions and the samples were incubated for 30 min at 37° C. The pH was then lowered to 4.4 by addition of 0.5 mL of 200 mM acetate buffer (pH 4.2, 100 mM KCl, 1 mM EDTA, 0.2% $NaN_3$) to each cuvette. The cuvettes were left undisturbed for 72 h at 37° C., then vortexed to evenly distribute any precipitate throughout the sample. The turbidity was measured on a Hewlett Packard model 8453 UV-Vis Spectrophotometer at 350 and 400, or 500 nm. All samples were performed in duplicate or triplicate and results reported are representative examples of at least three analyses.

Partitioning of Oxime Ether Inhibitors into TTR in Human Blood Plasma

The procedure for the antibody capture approach to evaluate inhibitor binding stoichiometry to TTR in human blood plasma has been described in detail elsewhere (Purkey, H. E.; et al. *Proc. Natl. Acad. Sc. U.S.A* 2001, 98, 5566-5571). Briefly, human blood plasma (1.5 mL) was added to a 2 mL eppendorf tube, followed by 7.5 µL of a 2.16 mM DMSO solution of test compound. This solution was incubated at 37° C. for 24 h, at which point 187 µL of a 1:1 (v:v) slurry of unfunctionalized sepharose resin in 10 mM Tris, (pH 8.0), 140 mM NaCl, 0.025% $NaN_3$ (TSA). This was incubated for another hour at 4° C., then centrifuged. The supernatant was divided into 3 aliquots of 400 µL, and each aliquot was added to 200 µL of a 1:1 slurry of sepharose resin conjugated to an anti-TTR antibody in TSA. After 20 min of gentle agitation at 4° C., the samples were centrifuged, the supernatant was removed, and the anti-TTR resin was washed with 1 mL TSA/0.05% Saponin (3×10 min) then 1 mL TSA (2×10 min) at 4° C. After centrifugation and removal of the supernatant, 155 µL of 100 mM triethylamine (pH 11.5) was added to dissociate the TTR and bound test compound from the resin-bound antibodies. After 30 min, the suspension was centrifuged and 145 µL of the supernatant, containing TTR and test compound, was removed. The supernatant (135 µL) was then injected onto an HPLC to determine the stoichiometry of small molecule binding to TTR. Under HPLC conditions, the test compound-TTR complex dissociates and the small molecule and protein can be separated. HPLC conditions: Keystone 3 cm C18 reverse phase column using either a 20-100% or 40-100% solvent B gradient over 8 min (solvent A: 95:5 $H_2O:CH_3CN$, 0.25% TFA; solvent B: 5:95 $H_2O:CH_3CN$, 0.25% TFA). The test compound and TTR quantification can be achieved by comparing the chromatogram integrated peak areas to standard curves; the ratio of the amount of test compound to TTR yields the binding stoichiometry (Purkey, H. E.; et al. *Proc. Natl. Acad. Sci. U.S.A* 2001, 98, 5566-5571).

Analytical Ultracentrifugation: Sedimentation Velocity Profile Analysis of TTR under Fibril Formation Conditions in the Presence of Oxime Ether Based Inhibitors Sedimentation analyses were performed at pH 4.4 on samples used previously in the fibril formation assay (see above). The sedimentation properties of recombinant WT-TTR solutions in the presence and absence of oxime ether inhibitor 8f were analyzed on a temperature controlled Beckman XL-I analytical ultracentrifuge equipped with an An60Ti rotor and photoelectric scanner. Data were collected at speeds of 3,000 and 50,000 rpm in continuous mode at 20° C., employing a step size of 0.001 cm, with detection at 280 nm.

A direct boundary fitting approach was applied to evaluate the sedimentation velocity data derived from a 3.6 µM TTR solution incubated with 7.2 µM of 8f at pH 4.4. The program Svedberg was used to fit multiple concentration vs. radial position data sets simultaneously to yield approximate solutions to the Lamm equation (Schuster, T. M.; Laue, T. M.; Editors *Modern Analytical Ultracentrifugation: Acquisition and Interpretation of Data for Biological and Synthetic Polymer Systems*; Birkhauser: Boston, 1994). The fitting algorithm yields the sedimentation coefficient and diffusion coefficient which affords the molecular weight using the following equation (Schuster, T. M.; Laue, T. M.; Editors *Modern Analytical Ultracentrifugation: Acquisition and Interpretation of Data for Biological and Synthetic Polymer Systems*; Birkhauser: Boston, 1994):

$$MW = \frac{sRT}{D(1-\bar{v}\rho)}$$

where MW is the molecular weight (Da), s is the sedimentation coefficient (in Svedbergs, $10^{-13}$ s), R is the universal gas constant ($8.314 \times 10^7$ erg/mol), $\bar{v}$ is the partial specific volume ($cm^3/g$), and π is the solvent density ($g/cm^3$). The buffer density D (1.00848 $g/cm^3$) was calculated from tabulated data and the partial specific volume of WT-TTR (0.7346 $cm^3/g$) was calculated from its amino acid composition.

Analytical Ultracentrifugation: Sedimentation Equilibrium Analysis of TTR under Fibril Formation Conditions in the Presence of Oxime Ether Based Inhibitors Sedimentation analyses were performed at pH 4.4 on samples used previously in the fibril formation assay (see above). Sedimentation equilibrium measurements were made by loading 120-140 µL of a solution of TTR (3.6 µM) and oxime ether 8f (7.2 mM) into a double sector cell, equipped with a 12-mm epon centerpiece and sapphire or quartz windows. Data were collected initially at rotor speeds of 3,000 rpm to ensure the absence of large molecular weight oligomers, which would sediment out first, then at 17,000 rpm to establish an equilibrium across the cell. The sedimentation profiles, monitored between 285 and 290 nm at 3 h intervals, were overlaid to establish that equilibrium had been achieved. Data analysis was performed using a nonlinear least squares analysis in the Origin software package provided by Beckman. The data was fit by several different models, including a single ideal species and several multiple species models, to identify the simplest model that best fit the data. The following equation, corresponding to a single ideal species model, fit the data best based on the small differences between the theoretical data and the experimental data (ibid.):

$$A_r = e^{\left[\ln(A_o) + M\omega^2\left(1 - \frac{\bar{v}\rho}{RT}\right)(x^2 - x_o^2)\right]} + E$$

where $A_r$ is the absorbance at radius x, $A_o$ is the absorbance at a reference radius $x_o$ (usually the meniscus), $\bar{v}$ is the partial specific volume of the protein, r is the density of the solvent ($g/cm^3$), ω is the angular velocity of the rotor (radian/sec), E is the baseline error correction factor, M is the molecular weight, and R is the universal gas constant. The differences between the experimental data points and the fitted data points (the residuals) were randomly distributed and small in magnitude (when the data was fit to a single ideal species model (TTR tetramer). Other models did not fit the data well as discerned by the non-random distribution of residuals across the cell.

WT-TTR.(5d)$_2$ Crystallization and X-ray Data Collection

WT-TTR crystals were obtained from 7 mg/mL protein solutions (100 mM KCl, 1 mM EDTA, 10 mM sodium phosphate, pH 7.0, 0.35-0.50 M ammonium sulfate) equilibrated against 2 M ammonium sulfate in hanging drop experiments. The TTR-(5d)$_2$ complexes were prepared from WT-TTR crystals soaked for more than three weeks with a 10-fold molar excess of inhibitor 5d. The crystals were placed in paratone oil as a cryo-protectant and cooled to 100 K. Data collection was performed using a Quantum-4 detector with a monochromatic high energy source of 14-BM-C, BIOCARS, Advance Photon Source. Crystals of TTR.(5d)$_2$ are isomorphous with the apo-TTR crystal form with unit cell dimensions close to a=43 Å, b=85 Å, and c=66 Å (space group P2$_1$2$_1$2 with two monomers in the asymmetric unit). Data were reduced with DENZO and SCALEPAC (Otwinowski, Z.; Minor, W. Macromolecular Crystallography, Part A. In *Methods in Enzymology*, 276: *Macromolecular Crystallography, Part A*; C. W. Carter, Jr. and R. M. Sweet, Eds.; Academic Press, 1997, 307-326).

WT-TTR.(5d)$_2$ Crystal Structure Determination and Refinement

The protein atomic coordinates for apo-TTR from the Protein Data Bank (accession number 1 BMZ) were refined by molecular dynamics and energy minimization protocols of the CNS against the 1.53 Å data set of TTR.(5d)$_2$ (Brunger, A. T.; et al. *Acta Crystallogr., Sect. D, Biol. Crystallogr.* 1998, 54, 905-921). The resulting difference Fourier maps showed significant electron densities in the outer binding cavity; however, inhibitor electron density in the inner cavity was only visible when the electron density maps were contoured below 1s, presumably due to flexibility in that region. Despite the weak linker density, the ligand could be unambiguously placed (because of the electron densities at the outer binding cavity) and was included in the crystallographic refinement. Due to the 2-fold crystallographic symmetry axis bisecting the binding channel, a statistical disorder model was applied, giving rise to two ligand binding modes per tetrameric TTR. After several cycles of simulated annealing and subsequent positional and temperature factor refinement, water molecules were placed into the difference Fourier maps. The final cycle of map fitting was done using the unbiased weighted electron density map calculated by the shake/warp bias removal protocol (Reddy, V.; et al. *Acta Crystallogr., Sect. D, Biol. Crystallogr.* 2003, 59, 2200-2210). Both the symmetry related binding conformations of the ligand in each binding pocket were in good agreement with unbiased annealed omit maps as well as the shake/warp unbiased weighted maps phased in the absence of the inhibitor. The final cycle of refinement was carried out by the maximum likelihood method using CCP4-Refmac (Bailey, S. *Acta Crystallogr., Sect. D, Biol. Crystallogr.* 1994, 50, 760-763; Murshudov, G. N.; et al. *Acta Crystallogr., Sect. D, Biol. Crystallogr.* 1997, 53, 240-255). The nine N-terminal and three C-terminal residues were not included in the final model because of the lack of interpretable electron densities in the final map. A summary of the crystallographic analysis data is presented in Table S4.

DETAILED DESCRIPTION OF FIGURES

FIG. 1 is a scheme showing the general approach for the formation of the bisaryloxime ether (X=O) and bisarylhydrazone (X=NH) libraries. This reaction could potentially produce two stereoisomers about the imine linkage (denoted syn and anti, i.e. the aldehyde proton could be oriented cis or trans, respectively, to the phenoxy oxygen represented by X); however, only the syn-isomer was expected (and observed, see text) based on literature precedent.

FIG. 2 shows the structures of aryloxyamine (1-8) and benzaldehyde (a-l) components used to synthesize the bisaryloxime ether library (see FIG. 1). The aryloxyamines chosen (1-8) had the same substitution patterns as the arylaldehydes, except for the absence of para-CF$_3$ (i) and the thyroxine-like substitution patterns (e and f) in the aryloxyamines. Unfortunately, the only commercially available aryloxyamine is phenoxyamine; thus, the methodology for the synthesis of the aryloxyamine building blocks required to prepare the bisaryloxime ether library was developed and disclosed herein.

Figure 3:
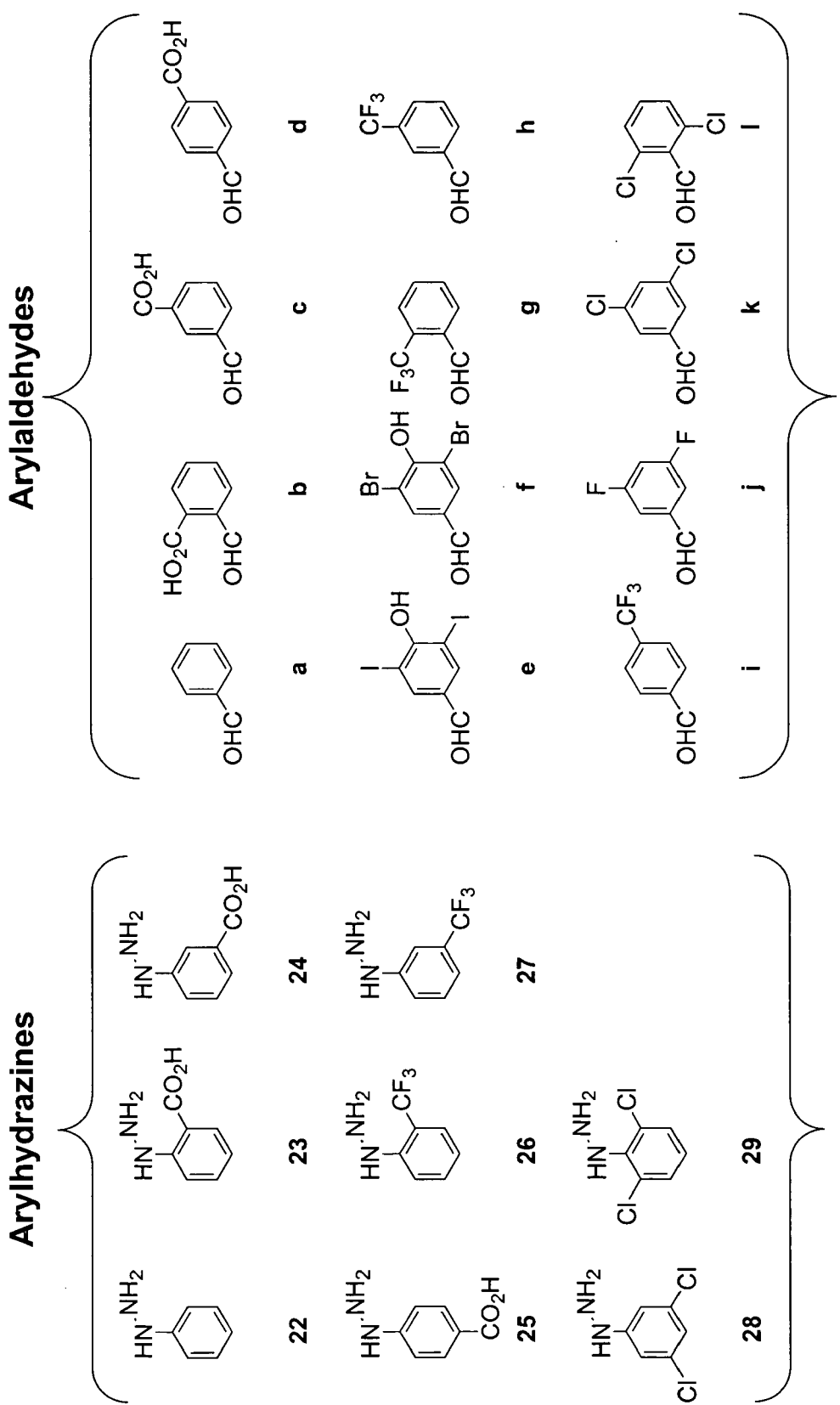
FIG. 3 illustrates the structures of the arylhydrazine (22-29) and benzaldehyde (a-l) compounds used to synthesize the bisarylhydrazone library.

FIG. 3 shows the structures of the arylhydrazine (22-29) and benzaldehyde (a-l) compounds used to synthesize the bisarylhydrazone library. The analogous bisaryloxime ethers and bisarylhydrazones (hereafter referred to as oxime ethers and hydrazones, respectively) were assumed to be isostructural with one another which is why this class was also synthesized.

FIG. 4 is a table showing the activities of the 96 bisarylhydrazones that were tested for inhibition of fibril formation. Bisarylhydrazone activity (7.2 µM) against WT-TTR (3.6 µM) amyloid fibril formation at pH 4.4 (72 h). Values represent the extent of fibril formation and thus inhibitor efficacy relative to WT-TTR fibril formation in the absence of inhibitor (assigned to be 100%): complete inhibition is equivalent to 0% fibril formation. Measurement error is ±5%. All inhibitors synthesized via high-throughput automation procedures displayed >95% purity by RP-LCMS with expected masses observed.

FIG. 5 shows the structures of the oxime ether and hydrazone inhibitors. Comparison of the oxime ether and hydrazone structures by crystallography reveal that the analogous compounds are nearly superimposable on one another. All four crystal structures display syn-imine linkages, further supporting the predominance of this isomer.

Figure 6:
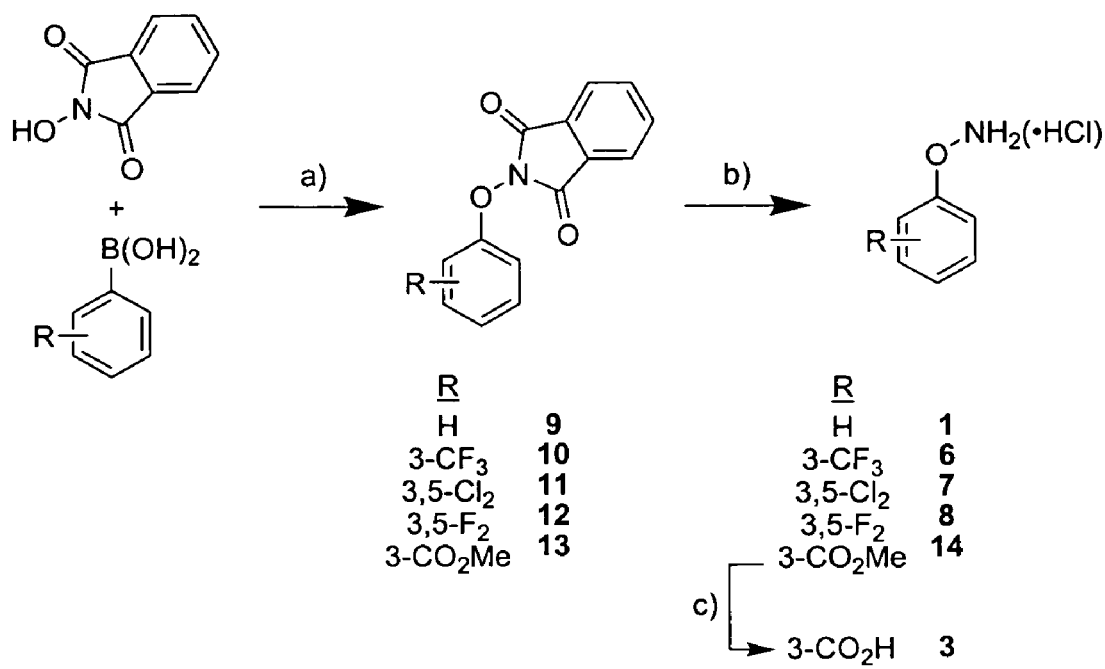
FIG. 6 illustrates a scheme for the synthesis of the required aryloxyamines.

FIG. 6 is a scheme for the synthesis of the required aryloxyamines. A copper-mediated cross-coupling of N-hydroxyphthalimide (NHP) with arylboronic acids affords the desired aryloxyamines after hydrazinolysis (Petrassi, H. M.; Sharpless, K. B.; Kelly, J. W. *Org. Lett.* 2001, 3, 139-142). Copper-mediated cross coupling of N-hydroxyphthalimide with arylboronic acids: a) CuCl, pyridine, 4 Å molecular sieves, 1,2-dichloroethane; b) H$_2$NNH$_2$.H$_2$O, 10% MeOH/CHCl$_3$; c) LiOH.H$_2$O, THF/MeOH/H$_2$O.

Figure 7:
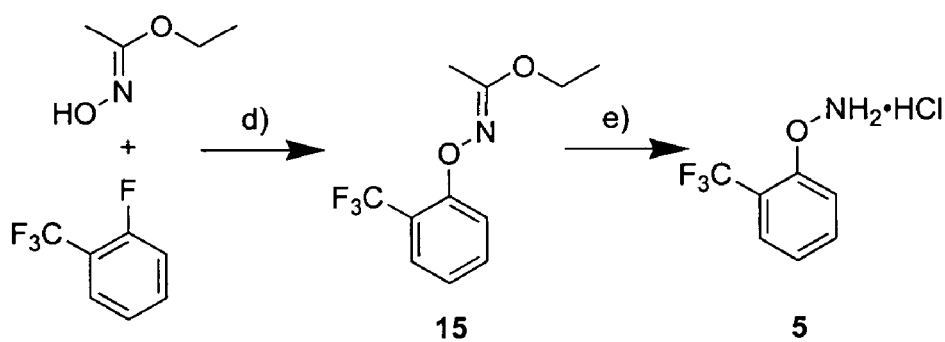
FIG. 7 illustrates a scheme for the synthesis of ortho-trifluoromethyl aryloxyamines.

FIG. 7 is a scheme for the synthesis of ortho-trifluoromethyl aryloxyamines. The synthesis requires the nucleophilic aromatic substitution of electron deficient flourobenzenes by ethyl-N-hydroxyacetimidate. (Miyazawa, E.; et al. *Org. Prep. Proced. Int.* 1997, 29, 594-600). Nucleophilic attack of ethyl-N-hydroxyacetimidate on 2-trifluoromethylflourobenzene gave an excellent yield of 15 (89%), which upon acidic hydrolysis gave aryloxyamine 5 (96% yield), utilized as its HCl salt. A variation on this methodology was used to prepare oxime ethers derived from the equivalents of 2 and 4 (see below). Nucleophilic aromatic substitution of electron deficient flourobenzenes by ethyl-N-hydroxyacetimidate: d) $^t$BuOK, DMF, 80° C.; e) HClO$_4$, 1,4-dioxane.

FIG. 8 is a table of the RP-HPLC purity of oxime ethers synthesized conventionally and isolated in mg quantities. Refer to experimental section for complete structural characterization data, including high-resolution MS and $^1$H- & $^{13}$C-NMR data. All inhibitors synthesized via high-throughput automation procedures displayed >95% purity by RP-LCMS with the expected masses observed.

FIG. 9 is a scheme showing the synthesis of bisaryloxime ethers by a trans-imination approach: a) Benzyl alcohol, DCC, cat. DMAP, CH$_2$Cl$_2$; b) Ethyl-N-hydroxyacetimidate, $^t$BuOK, DMF; c) LiOH.H$_2$O, THF/MeOH/H$_2$O; d) R'-benzaldehyde (a-l), 70% HClO$_4$, 1,4-dioxane. The arylacetimidates were not hydrolyzed to the corresponding aryloxyamines 2 and 4, instead they were mixed with stoichiometric amounts of arylaldehydes under acidic conditions to afford oxime ethers 2a-l and 4a-l directly in moderate to excellent yields (oxime ether 2b was not isolable due to instability).

FIG. 10 is a table summarizing the inhibitory activity of the oxime ethers (7.2 µM) against acid-mediated (pH 4.4) TTR (3.6 µM) amyloid formation. Of the 95 oxime ethers synthesized, 31 show good efficacy, reducing TTR amyloid formation to <10% of that exhibited by WT-TTR in the absence of inhibitor (90% inhibition, blue), 9 exhibit moderate activity (11-30% fibril formation, green), and the remaining 55 display poor activity (yellow). Oxime ethers derived from benzaldehydes with a thyroxine-like substitution pattern (rows e & f) are highly efficacious (all 16 displayed >90% inhibition), even when coupled with an unsubstituted phenoxyamine, a coupling that typically results in poor oxime ether inhibitors. These results challenge previous beliefs that appropriate substituents are required on both rings to achieve inhibition.

FIG. 11 is a table showing the percent oxime ether inhibitor remaining at the conclusion of the acid-mediated fibril formation assay (72 h). Inhibitor (7.2 µM) was incubated in the dark in the absence of, and with 3.6 µM WT-TTR (pH 4.4, 37° C.). The data for entry 5d* is under identical conditions except the buffer was maintained at pH 7.2. Values were determined by comparing inhibitor analytical RP-HPLC peak areas at the end of the assay to those obtained at the start of the assay. Measurement error is ±4%. The least stable inhibitors (1e, 1f, 2k, 3g, 5d*) undergo nearly complete degradation in the absence of TTR within 72 h; however, its presence maintains >74% of the initial dose. Notably, inhibitor 5e exhibits no decomposition in the presence of TTR. This helps explain why many of the labile bisaryloxime inhibitors prove to be excellent inhibitors of TTR amyloidogenesis: not only do the inhibitors bind to TTR's thyroid hormone binding sites and impose kinetic stabilization on the TTR tetramer (Hammarström, P.; et al. Science 2003, 299, 713-716), but TTR binding also stabilizes the inhibitors against degradation.

Figure 12:
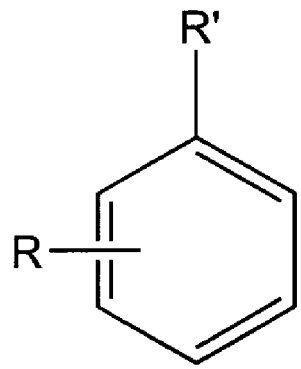
FIG. 12 illustrates a table showing inhibitory activity of the primary oxime ether and hydrazone decomposition and hydrolysis products (7.2 mM) against WT-TTR (3.6 mM) amyloid fibril formation at pH 4.4 (72 h).

FIG. 12 is a table showing inhibitory activity of the primary oxime ether and hydrazone decomposition and hydrolysis products (7.2 µM) against WT-TTR (3.6 µM) amyloid fibril formation at pH 4.4 (72 h). Values represent the extent of fibril formation and thus inhibitor efficacy relative to WT-TTR fibril formation in the absence of inhibitor (assigned to be 100%): complete inhibition is equivalent to 0% fibril formation. Measurement error is ±5%.

Figure 13:
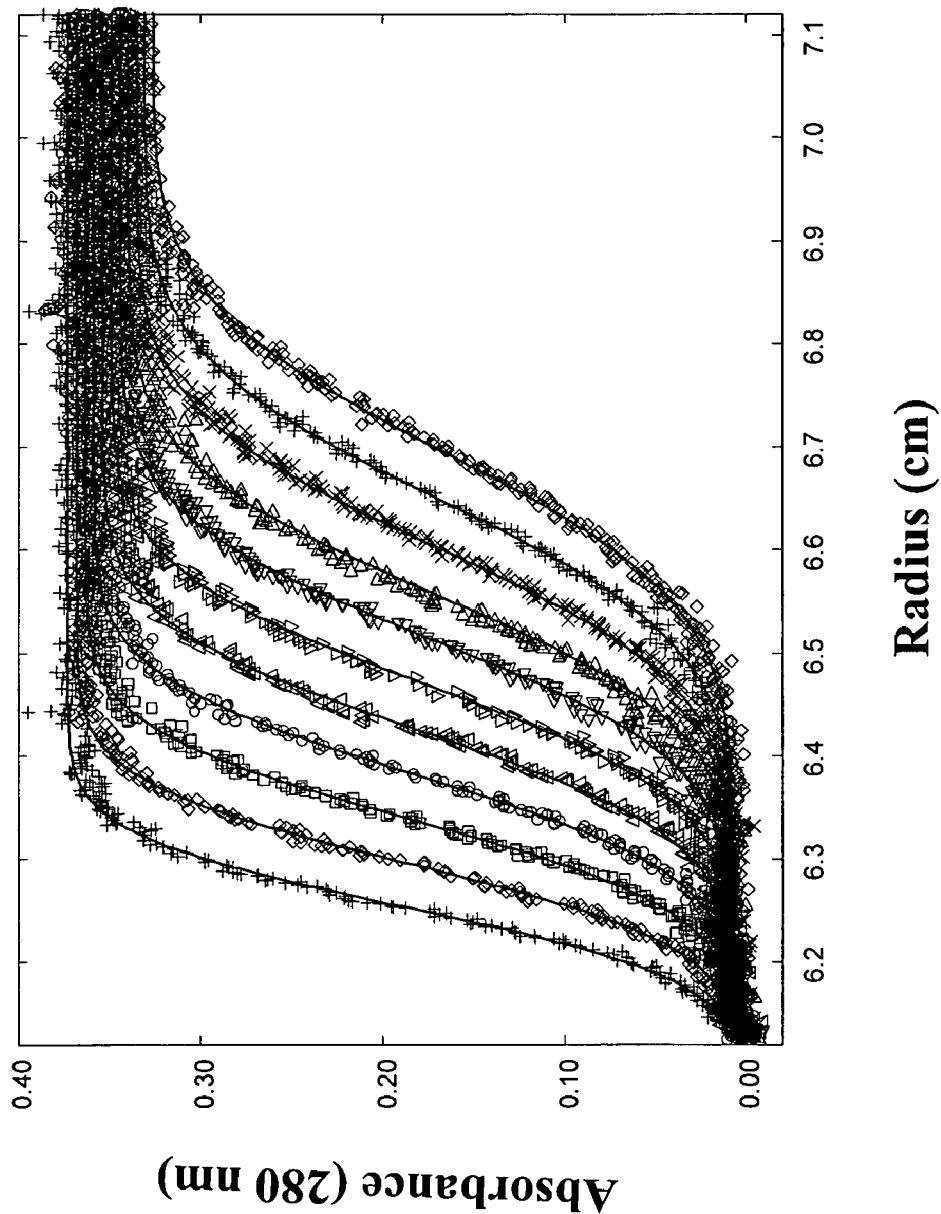
FIG. 13 illustrates a graph of sedimentation velocity (A) on TTR (3.6 mM) pre-incubated with 8f (7.2 mM; 30 min) and evaluated after a 72 h denaturation stress at pH 4.4.

FIG. 13 is a graph of sedimentation velocity (A) on TTR (3.6 µM) pre-incubated with 8f (7.2 µM; 30 min) and evaluated after a 72 h denaturation stress at pH 4.4. A. Velocity analysis—overlay of data sets taken at 50,000 rpm approximately 15 min apart. The data (symbols) fit to a single ideal species model (solid line) with MW 48.4±0.2 kDa.

Figure 14:
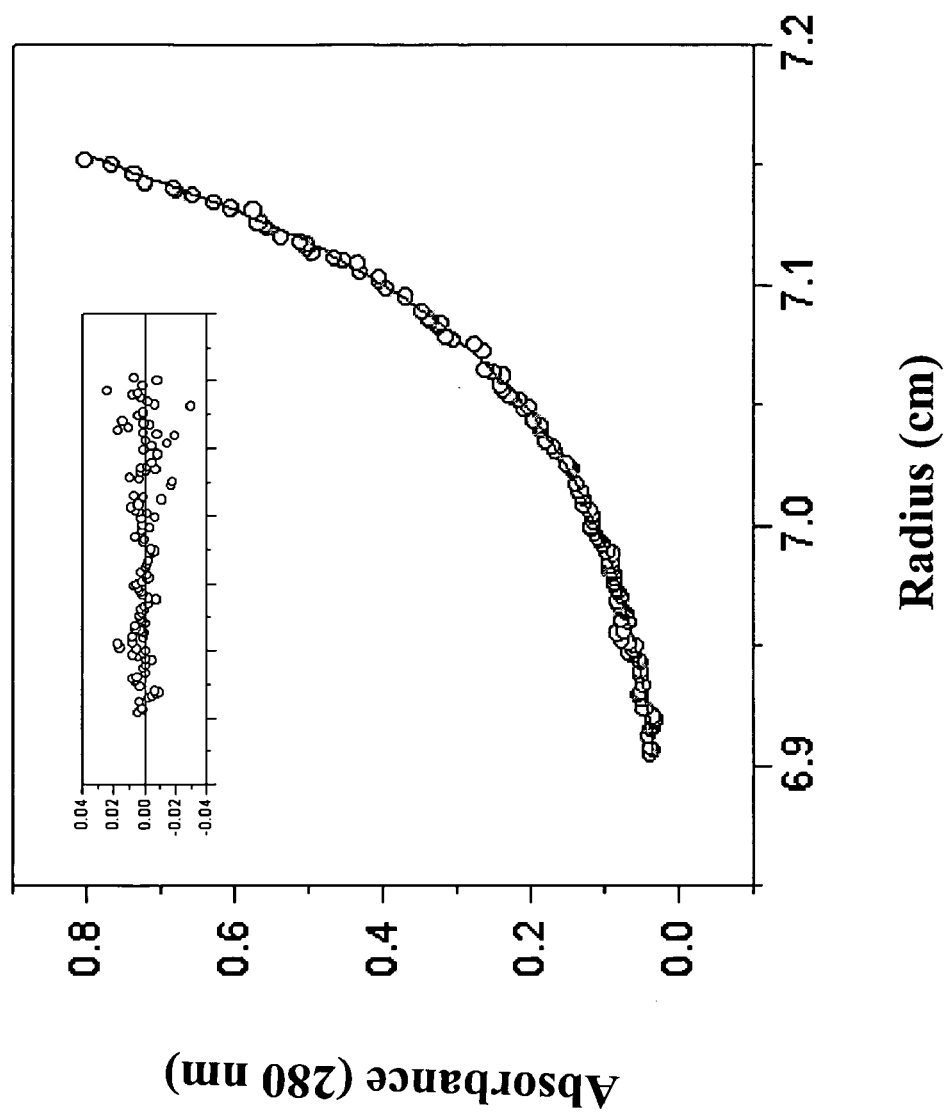
FIG. 14 illustrates a graph of equilibrium ultracentrifugation studies on TTR (3.6 mM) pre-incubated with 8f (7.2 mM; 30 min) and evaluated after a 72 h denaturation stress at pH 4.4.

FIG. 14 is a graph of equilibrium ultracentrifugation studies on TTR (3.6 µM) pre-incubated with 8f (7.2 µM; 30 min) and evaluated after a 72 h denaturation stress at pH 4.4. Equilibrium analysis—equilibrium concentration gradient observed after 24 h at a speed of 17,000 rpm. The data (o) fit to a single ideal species model (solid line) with MW 52.1±0.2 kDa. The residuals, the difference between experimental and fitted data, are shown in the inset.

FIG. 15 is a table showing the lower limits of the binding stoichiometry of bisaryloxime ethers displaying >90% amyloid inhibition (7.2 µM) to plasma TTR. Bisaryloxime ether binding stoichiometry to TTR in human blood plasma. TTR was treated with a variety of oxime ethers (10.8 µM) and the stoichiometry was determined by the antibody capture/HPLC method, which provides a minimum binding stoichiometry owing to wash associated losses (Purkey, H. E.; et al. Chemistry & Biology. In press; Purkey, H. E.; et al. Proc. Natl. Acad. Sci. U.S.A 2001, 98, 5566-5571). Of the 31 compounds tested, 11 exhibit TTR binding stoichiometries exceeding 1.0, with three showing greater than 1.5 equivalents bound. Oxime ethers exhibiting the highest binding stoichiometry are derived from aldehydes where one aromatic ring bears a thyroxine-like (e.g. 3,5-dihalo-4-hydroxy) substitution pattern. This result is very important because it implies that incorporation of a 3,5-dihalo-4-hydroxy substituted aryl ring imparts TTR plasma binding selectivity over the majority of other plasma proteins including the thyroxine transport protein albumin, which has a concentration ~150 times greater than that of TTR (Stockigt, J. R. Thyroid Hormone Binding and Metabolism. Endocrinology, Fourth Ed. Degroot, L. J., Jameson, J. L., Eds.; W.B. Saunders Co.: Philadelphia, 2001, Volume 2, Chapter 94, 1314-1326; Petitpas, I.; et al. Proc. Nat. Acad. Sci., U.S.A. 2003, 100, 6440-6445).

FIG. 16 shows a ribbon diagram depiction of bisaryloxime ether 5d bound to both of the WT-TTR thyroxine binding cavities (white boxes) based on X-ray crystallographic data. The expansion of one of the sites (top) shows 5d in both of its symmetry related binding modes (green and white), with the TTR binding site surface shown in gray. Key residues and halogen binding pockets (HBPs) are labeled; primed and unprimed residues or HBPs refer to two neighboring symmetry related monomers comprising the T$_4$ site. It appears that the carboxylate substituent in the outer binding pocket is making an electrostatic interaction with the Lys-15 ε-NH$_3^+$ group.

FIG. 17 shows the X-ray crystal structure data for WT-TTR soaked with oxime ether 5d.

What is claimed is:
1. A bisarylhydrazone selected from the following structures:
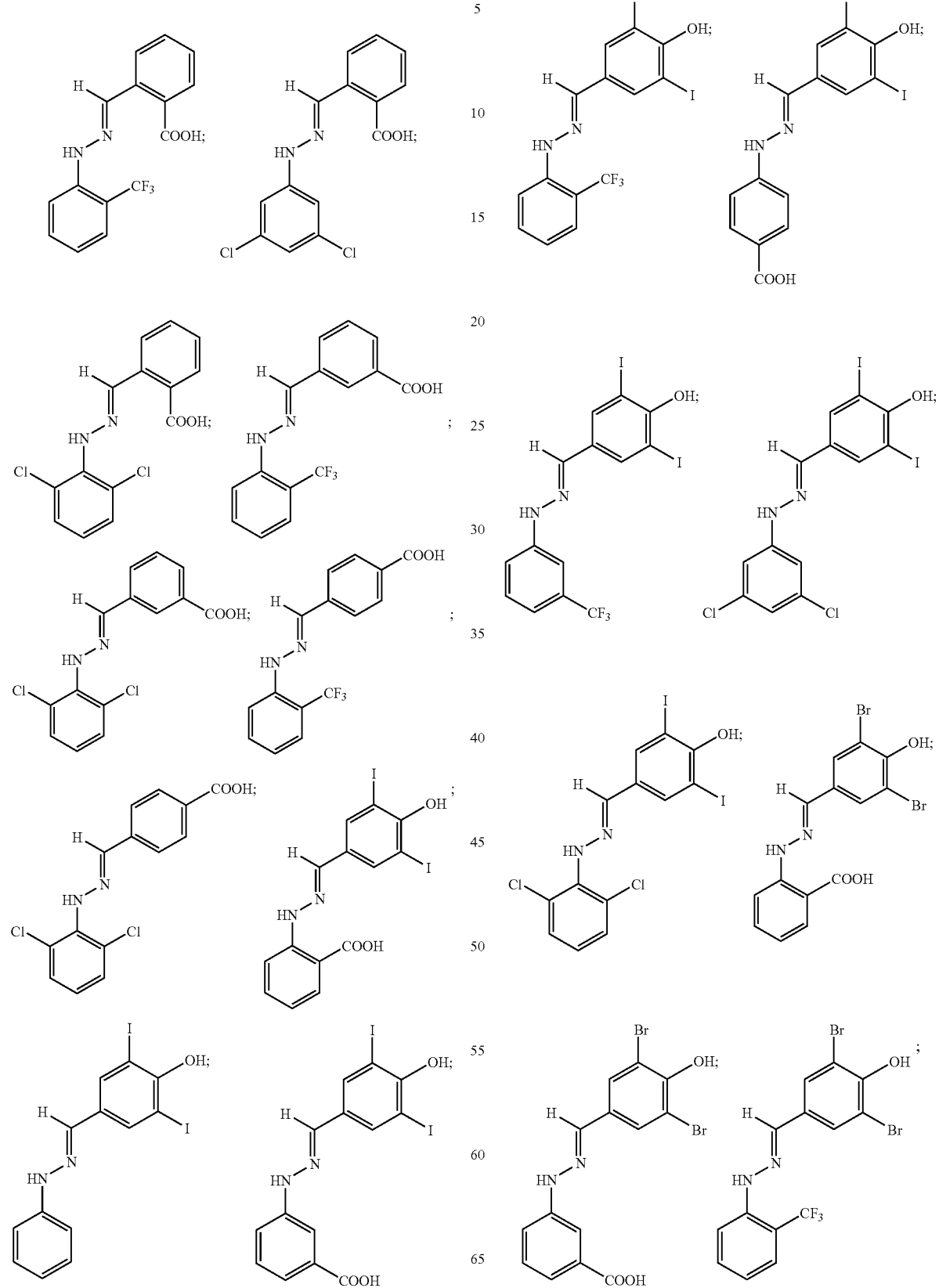

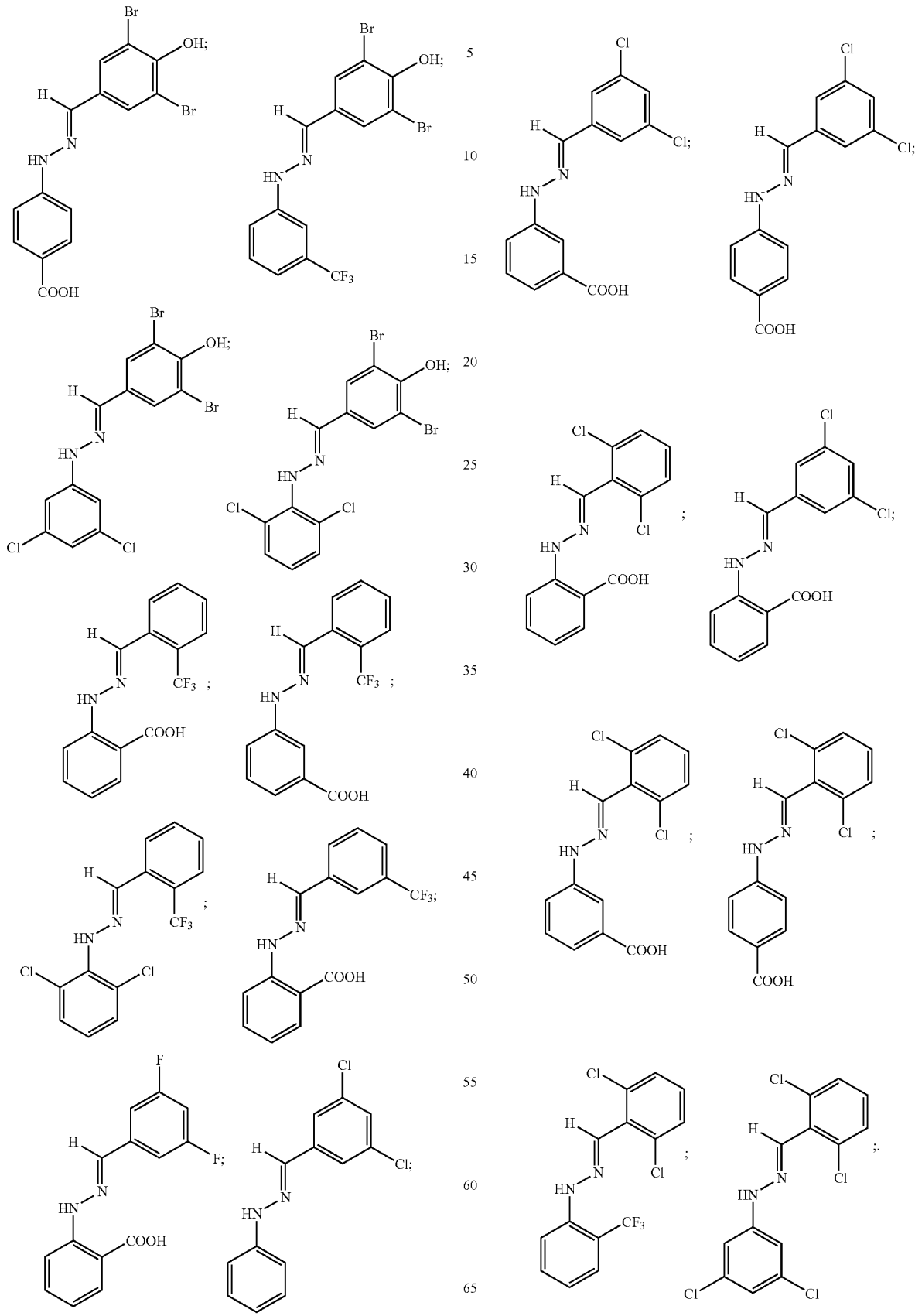

2. A bisarylhydrazone according to claim 1 having the following structure:

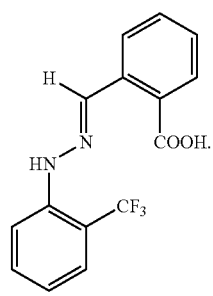

3. A bisarylhydrazone according to claim 1 having the following structure:

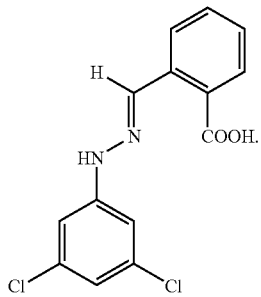

4. A bisarylhydrazone according to claim 1 having the following structure:

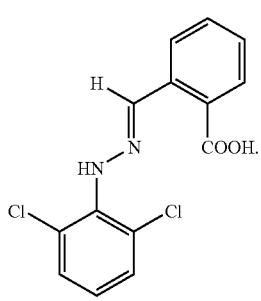

5. A bisarylhydrazone according to claim 1 having the following structure:

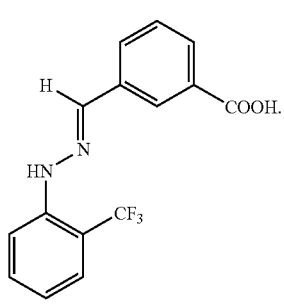

6. A bisarylhydrazone according to claim 1 having the following structure:

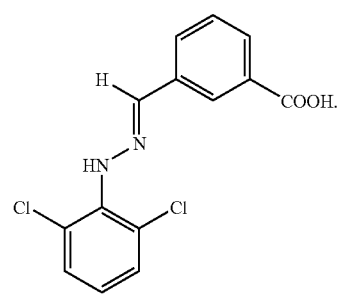

7. A bisarylhydrazone according to claim 1 having the following structure:

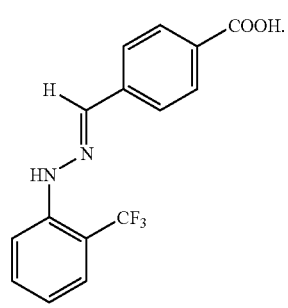

8. A bisarylhydrazone according to claim 1 having the following structure:

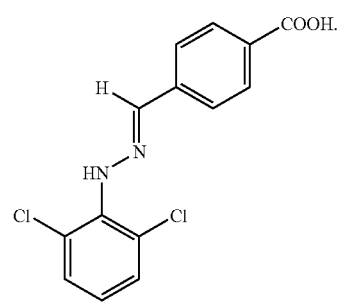

9. A bisarylhydrazone according to claim 1 having the following structure:

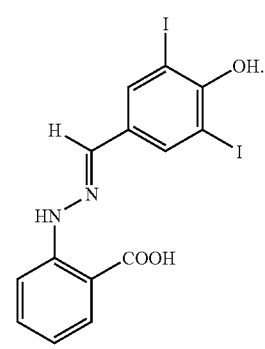

10. A bisarylhydrazone according to claim 1 having the following structure:

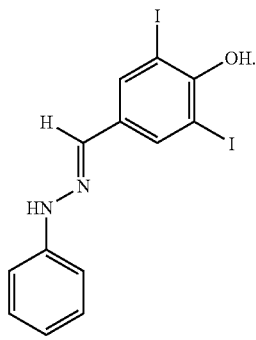

11. A bisarylhydrazone according to claim 1 having the following structure:

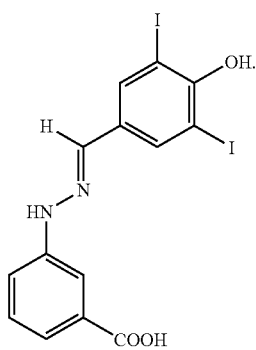

12. A bisarylhydrazone according to claim 1 having the following structure:

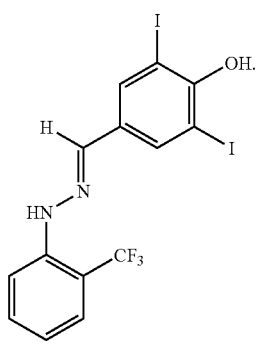

13. A bisarylhydrazone according to claim 1 having the following structure:

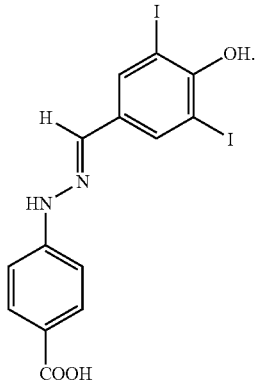

14. A bisarylhydrazone according to claim 1 having the following structure:

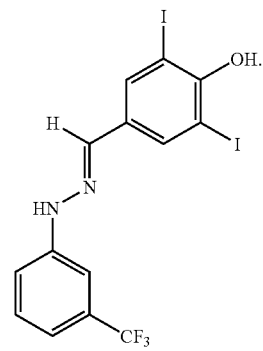

15. A bisarylhydrazone according to claim 1 having the following structure:

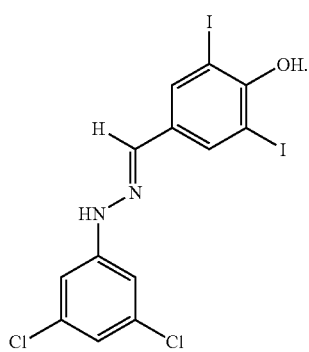

16. A bisarylhydrazone according to claim 1 having the following structure:

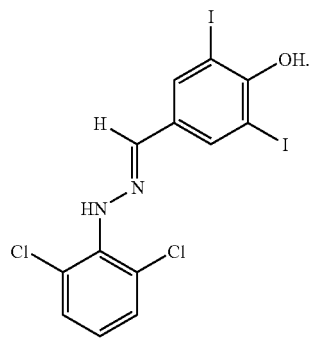

17. A bisarylhydrazone according to claim 1 having the following structure:

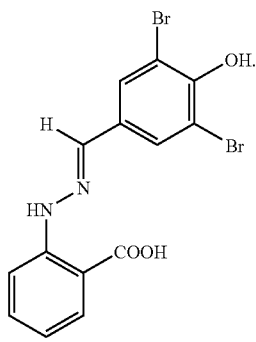

18. A bisarylhydrazone according to claim 1 having the following structure:

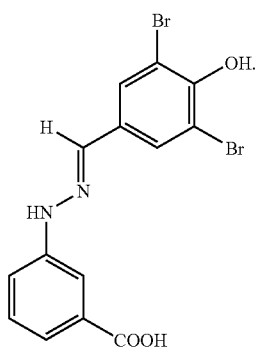

19. A bisarylhydrazone according to claim 1 having the following structure:

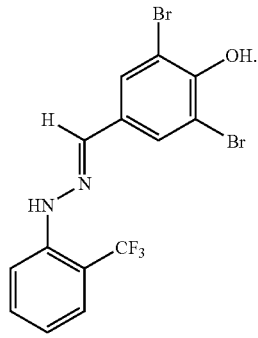

20. A bisarylhydrazone according to claim 1 having the following structure:

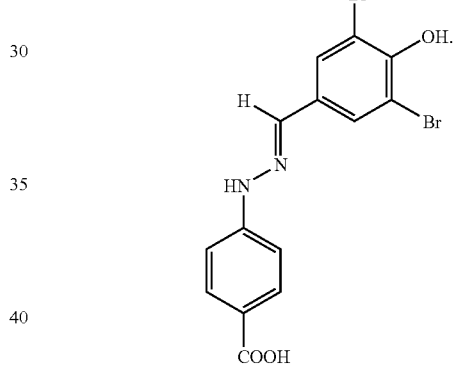

21. A bisarylhydrazone according to claim 1 having the following structure:

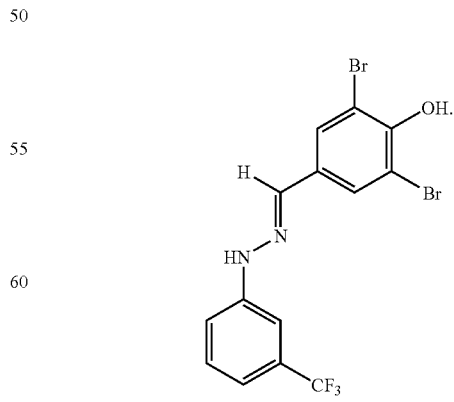

22. A bisarylhydrazone according to claim 1 having the following structure:

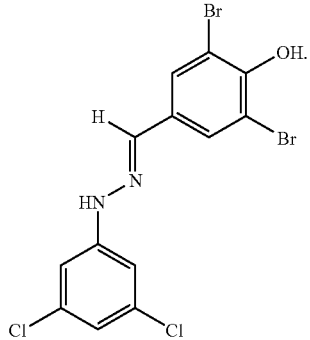

23. A bisarylhydrazone according to claim 1 having the following structure:

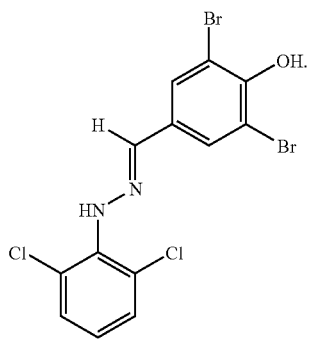

24. A bisarylhydrazone according to claim 1 having the following structure:

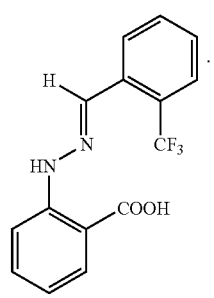

25. A bisarylhydrazone according to claim 1 having the following structure:

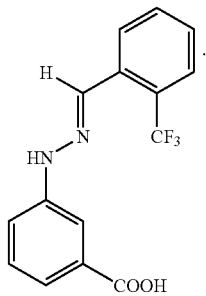

26. A bisarylhydrazone according to claim 1 having the following structure:

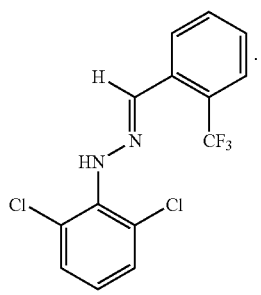

27. A bisarylhydrazone according to claim 1 having the following structure:

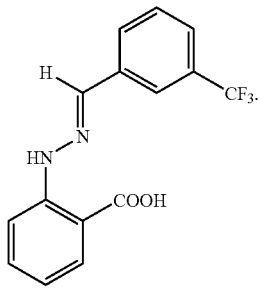

28. A bisarylhydrazone according to claim 1 having the following structure:

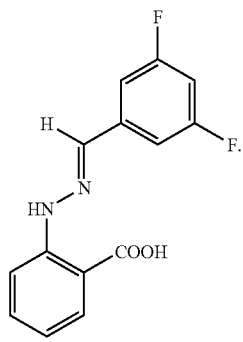

29. A bisarylhydrazone according to claim 1 having the following structure:

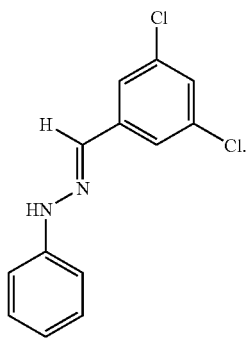

30. A bisarylhydrazone according to claim 1 having the following structure:

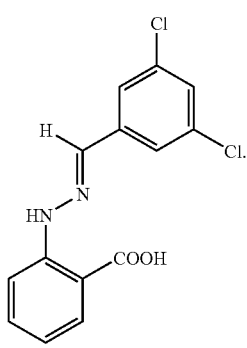

31. A bisarylhydrazone according to claim 1 having the following structure:

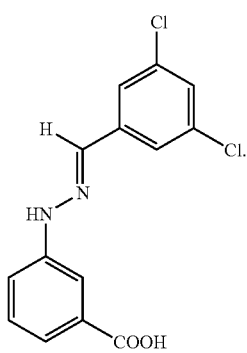

32. A bisarylhydrazone according to claim 1 having the following structure:

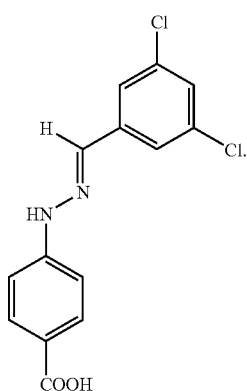

33. A bisarylhydrazone according to claim 1 having the following structure:

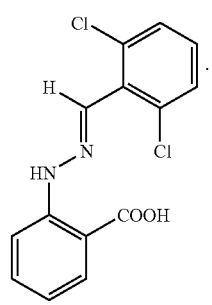

34. A bisarylhydrazone according to claim 1 having the following structure:

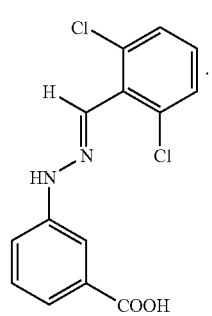

35. A bisarylhydrazone according to claim 1 having the following structure:
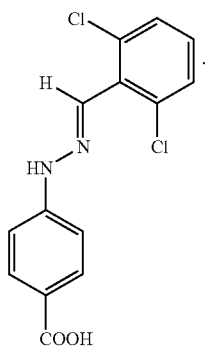
36. A bisarylhydrazone according to claim 1 having the following structure:
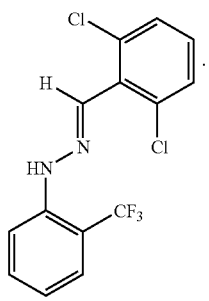
37. A bisarylhydrazone according to claim 1 having the following structure:
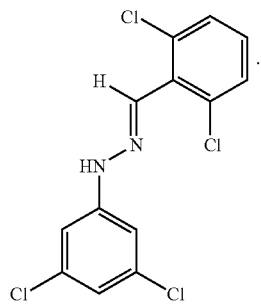
38. A bisaryloxime ether selected from the following structures:
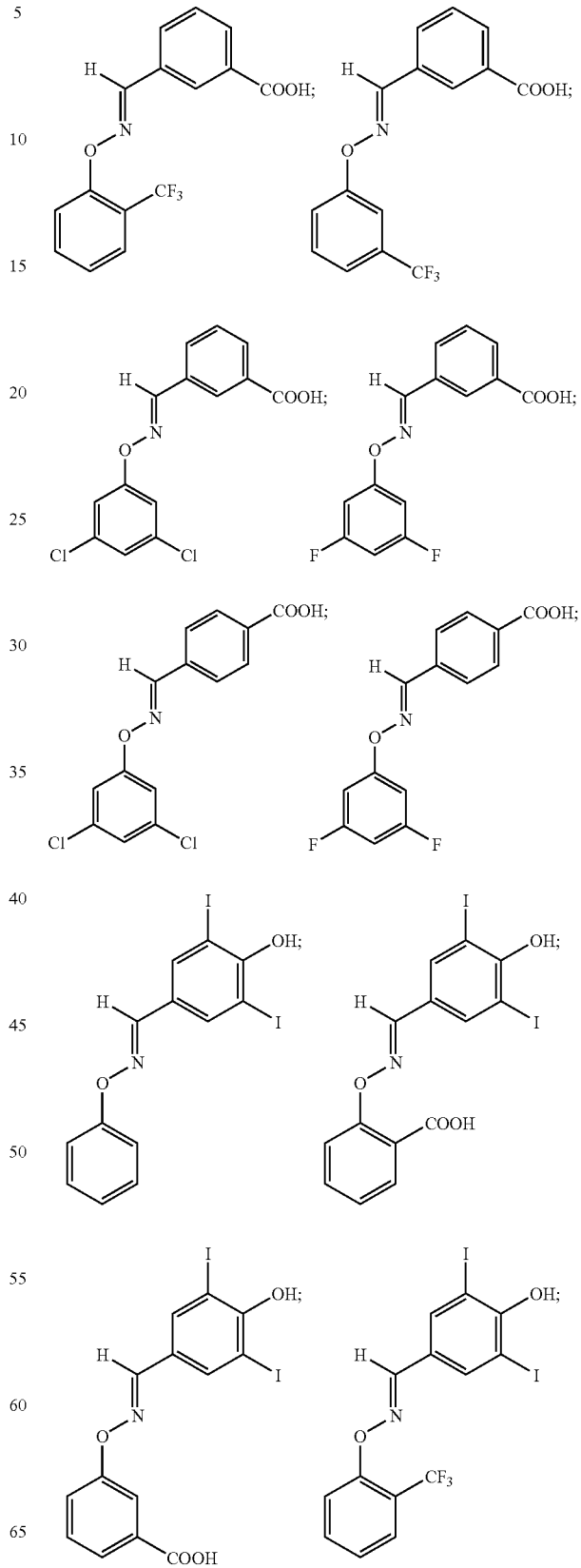

-continued
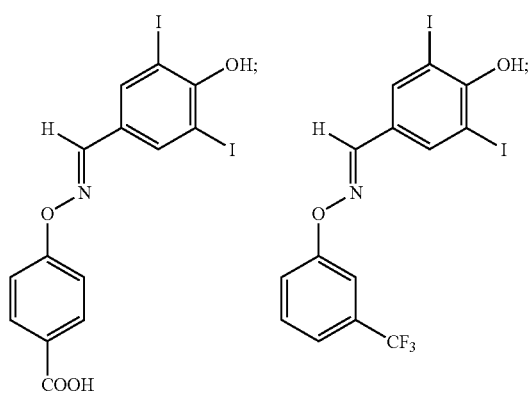
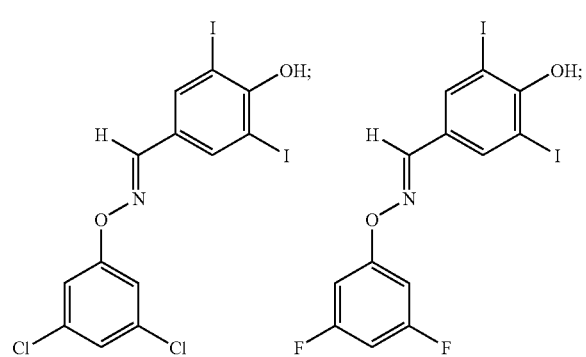
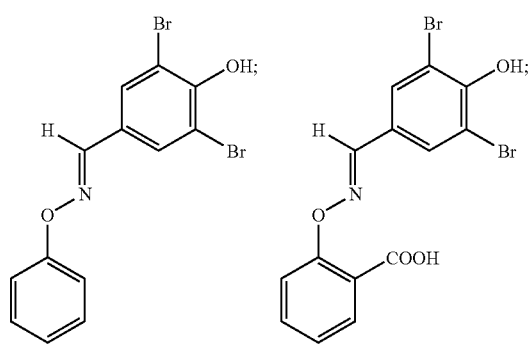
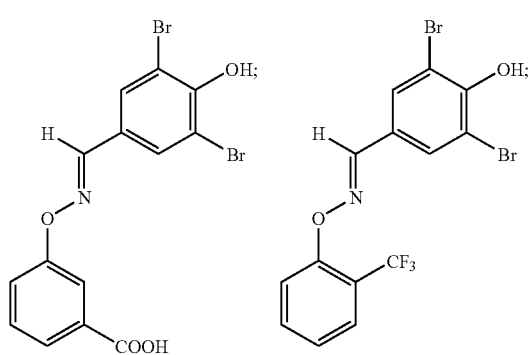
-continued
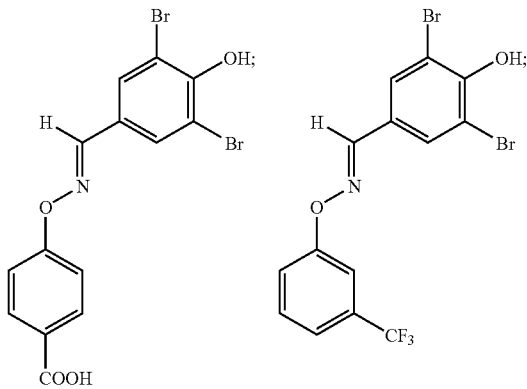
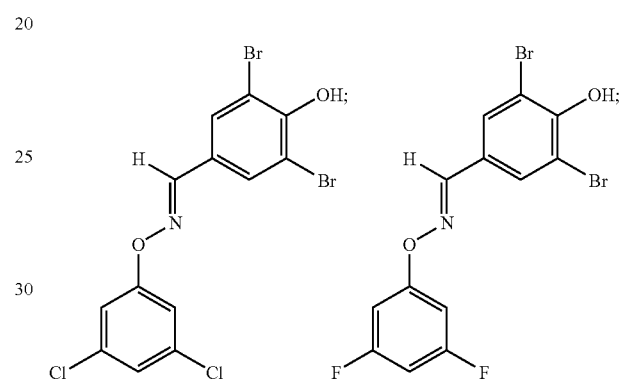
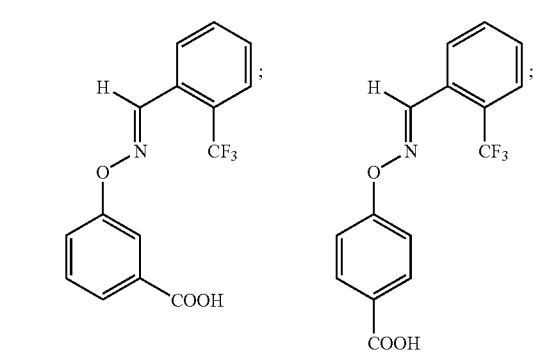
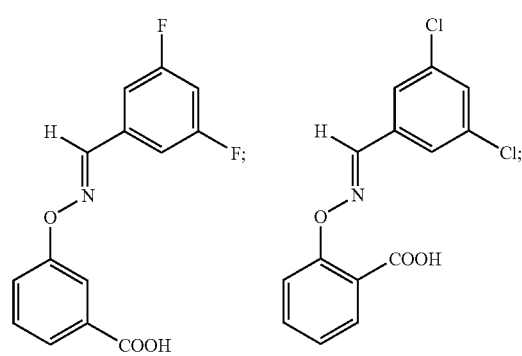

-continued

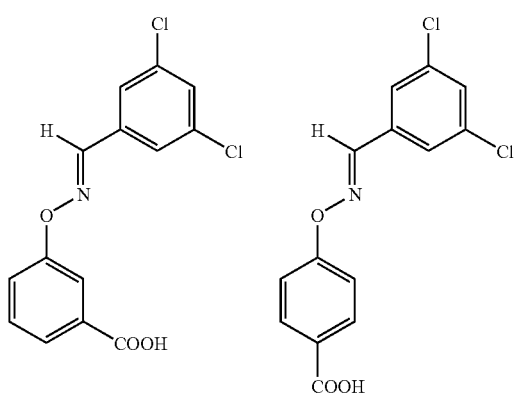

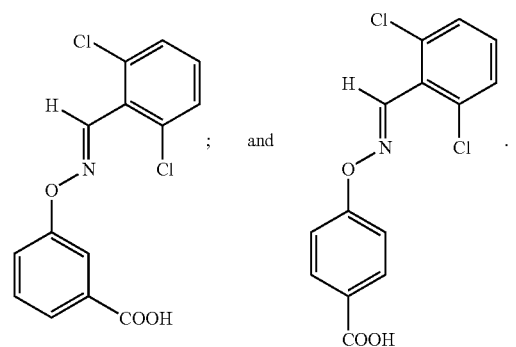 ; and

39. A bisaryloxime ether according to claim 38 having the following structure:

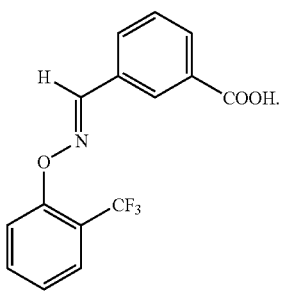

40. A bisaryloxime ether according to claim 38 having the following structure:

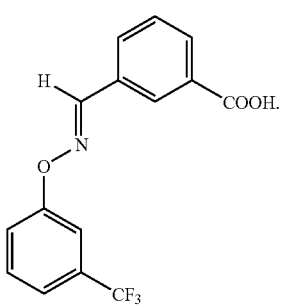

41. A bisaryloxime ether according to claim 38 having the following structure:

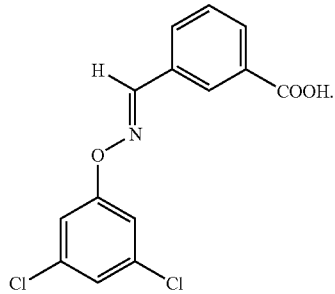

42. A bisaryloxime ether according to claim 38 having the following structure:

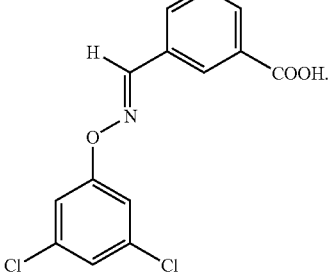

43. A bisaryloxime ether according to claim 38 having the following structure:

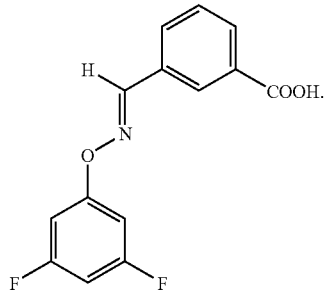

44. A bisaryloxime ether according to claim 38 having the following structure:

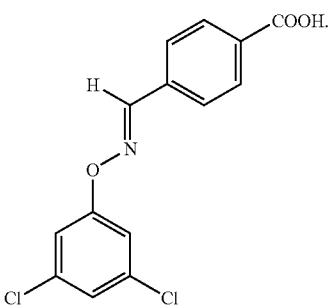

45. A bisaryloxime ether according to claim 38 having the following structure:

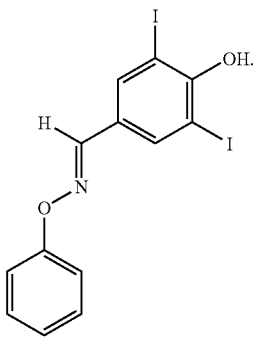

46. A bisaryloxime ether according to claim 38 having the following structure:

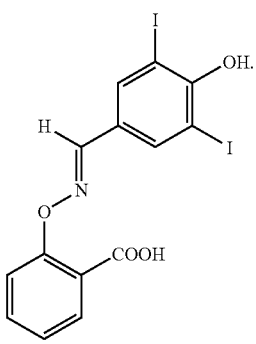

47. A bisaryloxime ether according to claim 38 having the following structure:

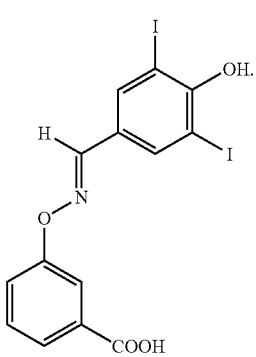

48. A bisaryloxime ether according to claim 38 having the following structure:

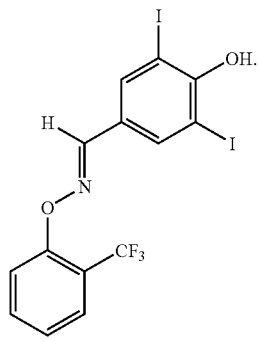

49. A bisaryloxime ether according to claim 38 having the following structure:

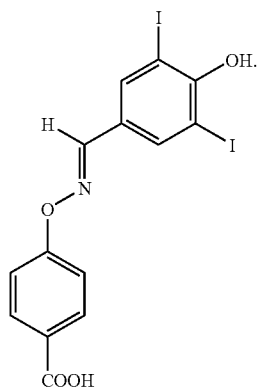

50. A bisaryloxime ether according to claim 38 having the following structure:

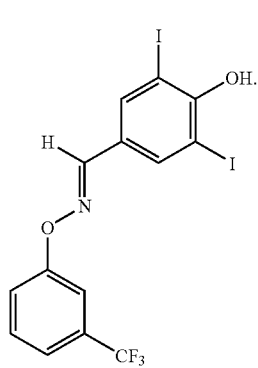

51. A bisaryloxime ether according to claim 38 having the following structure:

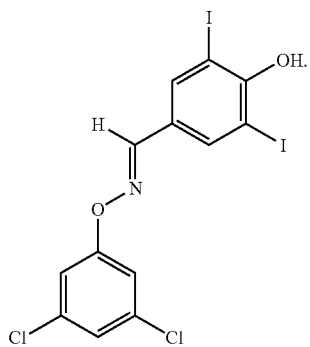

52. A bisaryloxime ether according to claim 38 having the following structure:

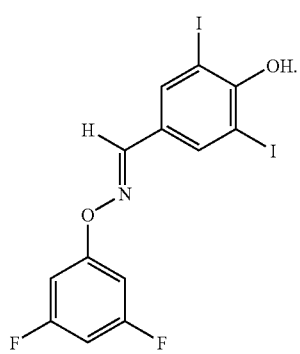

53. A bisaryloxime ether according to claim 38 having the following structure:

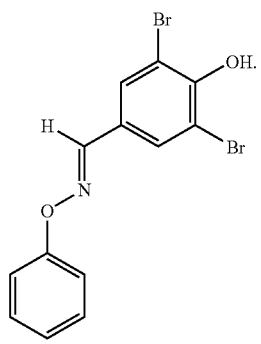

54. A bisaryloxime ether according to claim 38 having the following structure:

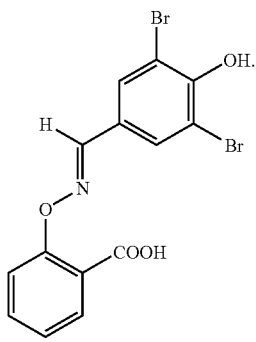

55. A bisaryloxime ether according to claim 38 having the following structure:

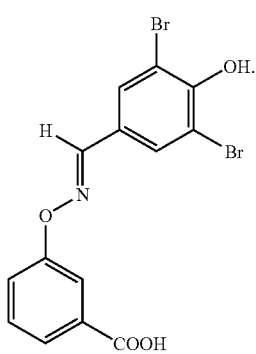

56. A bisaryloxime ether according to claim 38 having the following structure:

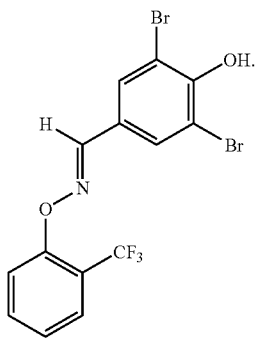

57. A bisaryloxime ether according to claim 38 having the following structure:

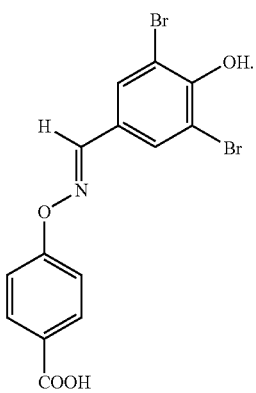

58. A bisaryloxime ether according to claim 38 having the following structure:

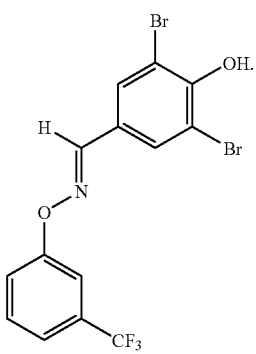

59. A bisaryloxime ether according to claim 38 having the following structure:

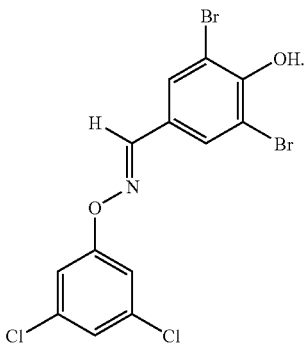

60. A bisaryloxime ether according to claim 38 having the following structure:

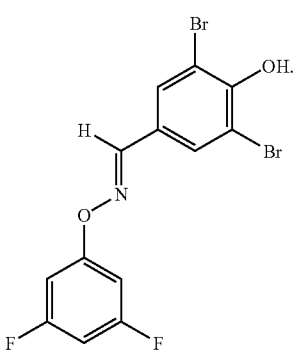

61. A bisaryloxime ether according to claim 38 having the following structure:

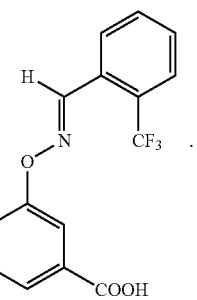

62. A bisaryloxime ether according to claim 38 having the following structure:

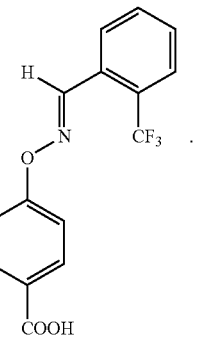

63. A bisaryloxime ether according to claim 38 having the following structure:

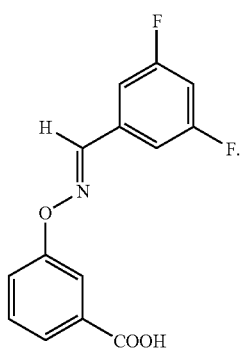

64. A bisaryloxime ether according to claim 38 having the following structure:

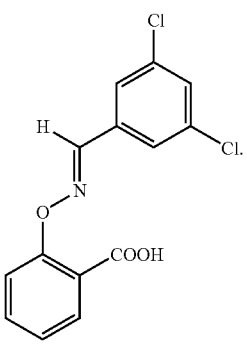

65. A bisaryloxime ether according to claim 38 having the following structure:

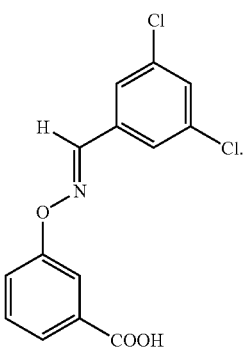

66. A bisaryloxime ether according to claim 38 having the following structure:

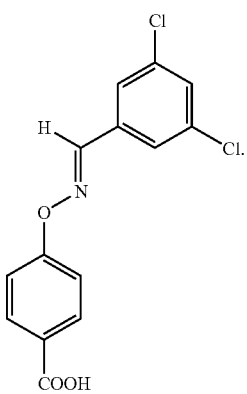

67. A bisaryloxime ether according to claim 38 having the following structure:

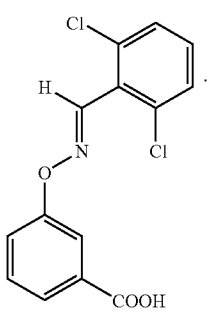

68. A bisaryloxime ether according to claim 38 having the following structure:

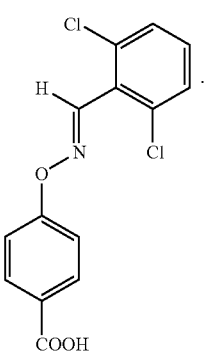

* * * * *